US012285369B2

(12) United States Patent
Forst et al.

(10) Patent No.: US 12,285,369 B2
(45) Date of Patent: Apr. 29, 2025

(54) HEAD STABILIZATION DEVICE WITH DETACHABLE TORQUE APPLICATOR

(71) Applicant: pro med instruments GmbH, Freiburg im Breisgau (DE)

(72) Inventors: Peter Forst, Emmendingen (DE); David Devran Culha, Eschbach (DE); Marco Stephan Willesch, Eichstetten (DE); Matthias Edgar Schuele, Freiburg (DE); Matthias Esser, Freiburg (DE); Jan Heiko Mertens, Freiburg (DE)

(73) Assignee: pro med instruments, GmbH, Freiburg im Breisgau (DE)

( * ) Notice: Subject to any disclaimer, the term of this patent is extended or adjusted under 35 U.S.C. 154(b) by 605 days.

(21) Appl. No.: 16/952,504

(22) Filed: Nov. 19, 2020

(65) Prior Publication Data
US 2021/0154076 A1    May 27, 2021

Related U.S. Application Data

(60) Provisional application No. 62/939,053, filed on Nov. 22, 2019.

(51) Int. Cl.
*A61G 13/00* (2006.01)
*A61B 90/14* (2016.01)
*A61G 13/12* (2006.01)

(52) U.S. Cl.
CPC ............ *A61G 13/121* (2013.01); *A61B 90/14* (2016.02)

(58) Field of Classification Search
CPC .... A61G 13/121; A61G 13/101; A61G 13/10; A61B 90/14; A61B 90/16; A61B 90/17;
(Continued)

(56) References Cited

U.S. PATENT DOCUMENTS 4,758,754 A     7/1988  Fink et al.
4,838,264 A *   6/1989  Bremer ................. A61B 6/12
                                                    606/86 R
(Continued)

FOREIGN PATENT DOCUMENTS

EP      2 903 554 A1     8/2015
JP      2002-524191 A    8/2002
WO      WO 2004/071320 A1 8/2004

OTHER PUBLICATIONS

Mayfield Radiolucent Solutions: Meeting Intraoperative Imaging Needs in the Neurosurgical Operating Room; downloaded from mayfield-radiolucent-solutions.pdf (cardion.cz), accessed on Mar. 8, 2021; 12 pgs.

*Primary Examiner* — Adam Baker
(74) *Attorney, Agent, or Firm* — Frost Brown Todd LLP

(57) ABSTRACT

A head stabilization device includes a stabilization assembly and an applicator to control an amount of force that a stabilization feature applies to the head of the patient. The applicator includes a torque control feature that ensures a desired torque setting is not exceeding during use. The applicator can be detached from the remainder of the system such that the head stabilization device is usable without having a connected torque controlling feature or structures. The applicator in one version controls torque by adjusting a bending length of a pair of arms that extend within the applicator.

15 Claims, 16 Drawing Sheets

(58) Field of Classification Search
CPC ......... A61B 90/18; A61B 90/50; A61B 90/57;
A61B 90/25; A61B 90/11; A61B 90/30;
A61B 2090/571; A61B 2090/031; A61B
17/885; A61B 17/8866; B25B 23/141;
B25B 23/14; F16D 7/06; F16D 7/04
USPC .......................................... 128/845; 606/104
See application file for complete search history.

(56) References Cited

U.S. PATENT DOCUMENTS

| | | | | |
|---|---|---|---|---|
| 5,318,509 | A * | 6/1994 | Agbodoe | A61B 90/14 |
| | | | | 5/643 |
| 5,537,704 | A * | 7/1996 | Dinkler | A61B 90/14 |
| | | | | 5/643 |
| 5,746,298 | A | 5/1998 | Krivec et al. | |
| 7,507,244 | B2 | 3/2009 | Dinkler | |
| 7,730,563 | B1 * | 6/2010 | Sklar | A61G 13/121 |
| | | | | 5/640 |
| 9,695,882 | B2 * | 7/2017 | Jakoubek | F16D 7/048 |
| 2002/0151907 | A1 * | 10/2002 | Day | A61B 90/14 |
| | | | | 606/151 |
| 2005/0075650 | A1 * | 4/2005 | Dinkler | A61B 90/14 |
| | | | | 606/130 |
| 2007/0250071 | A1 * | 10/2007 | Soerensen | A61B 90/14 |
| | | | | 606/130 |
| 2013/0190604 | A1 * | 7/2013 | Moffatt | A61B 6/4441 |
| | | | | 600/411 |
| 2015/0020817 | A1 | 1/2015 | Radina et al. | |
| 2019/0053967 | A1 | 2/2019 | Moosmann et al. | |

* cited by examiner

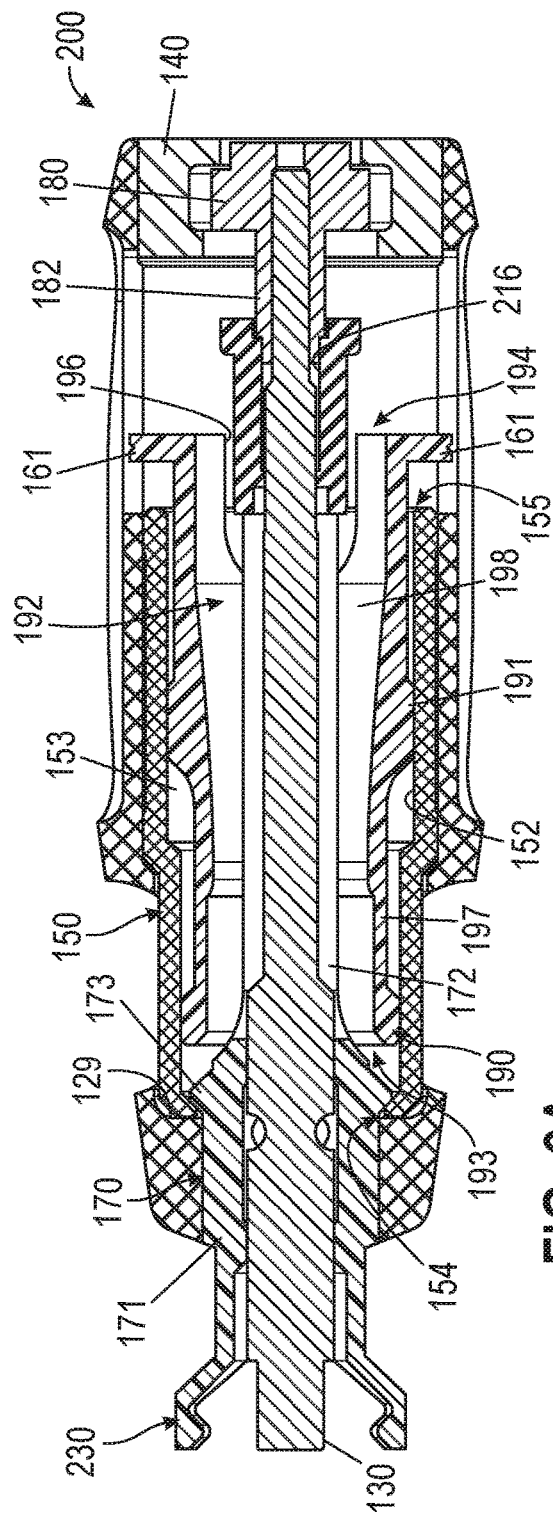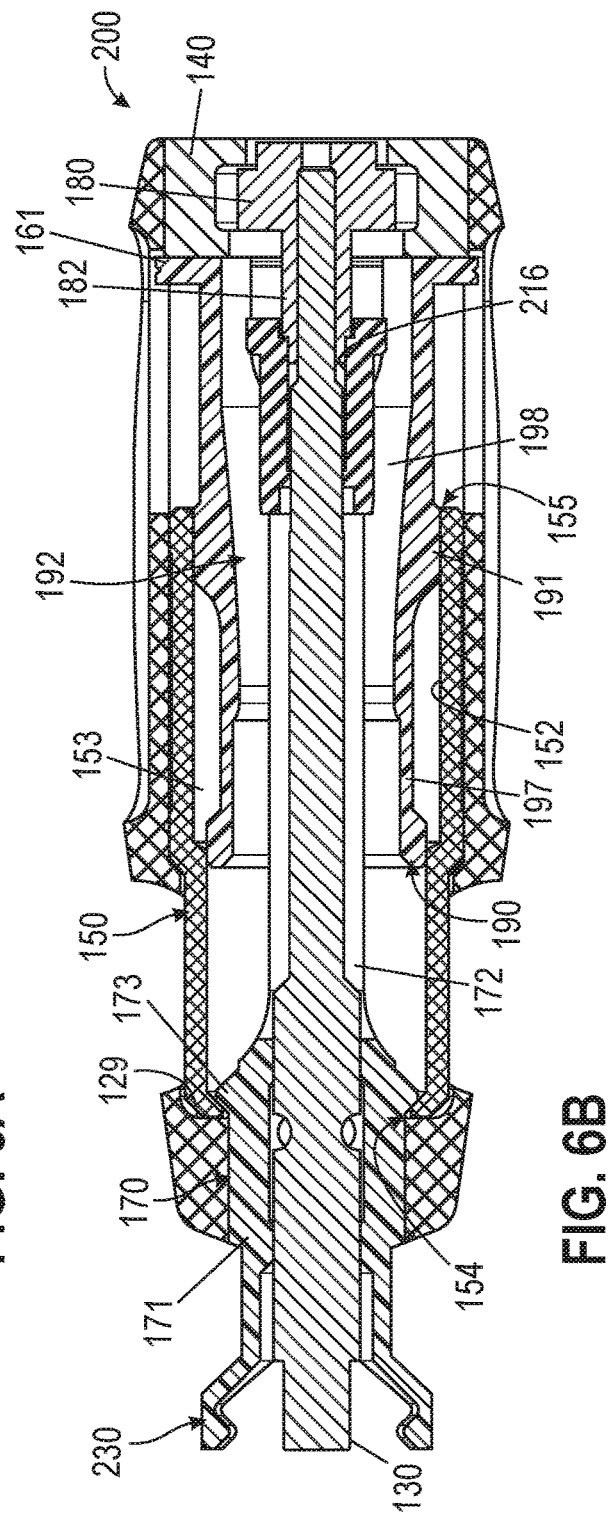

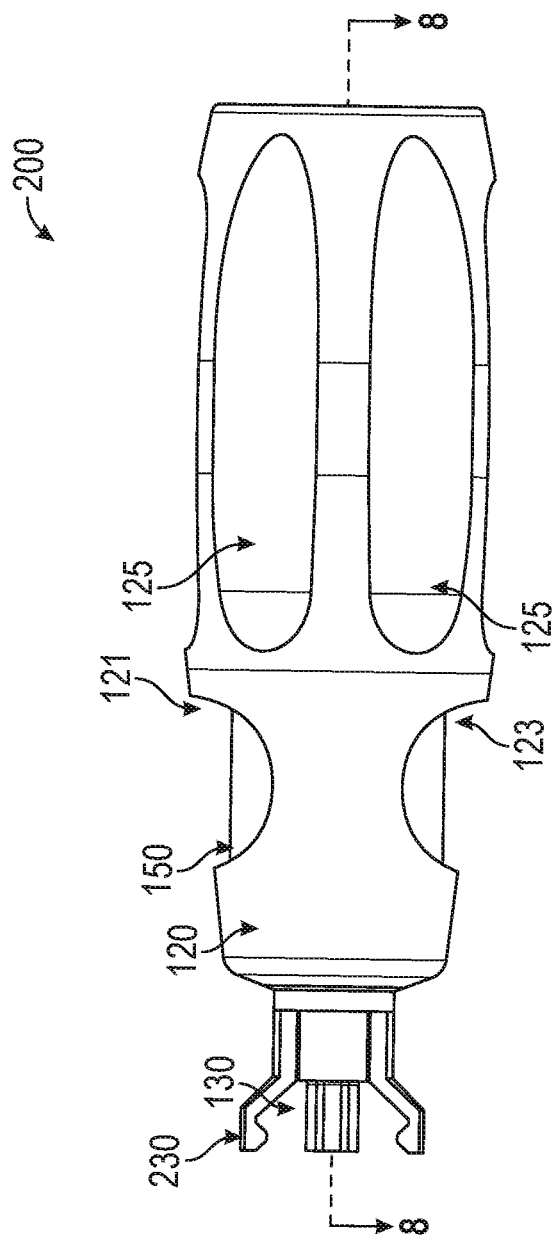

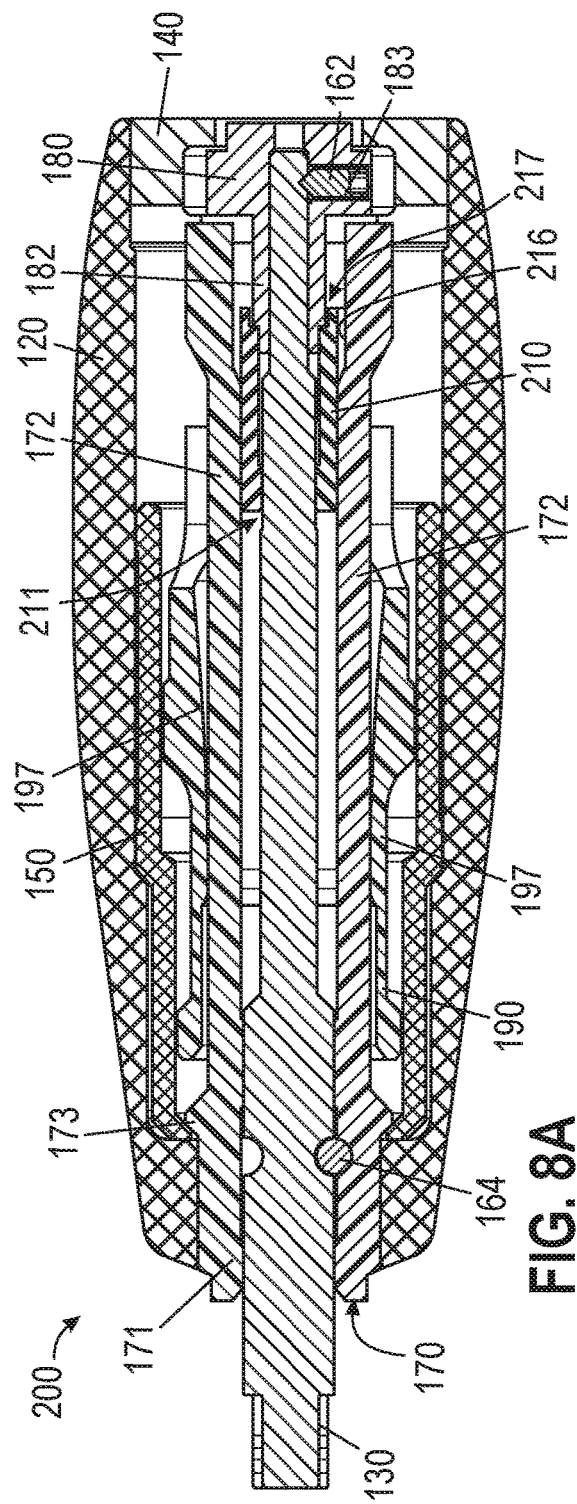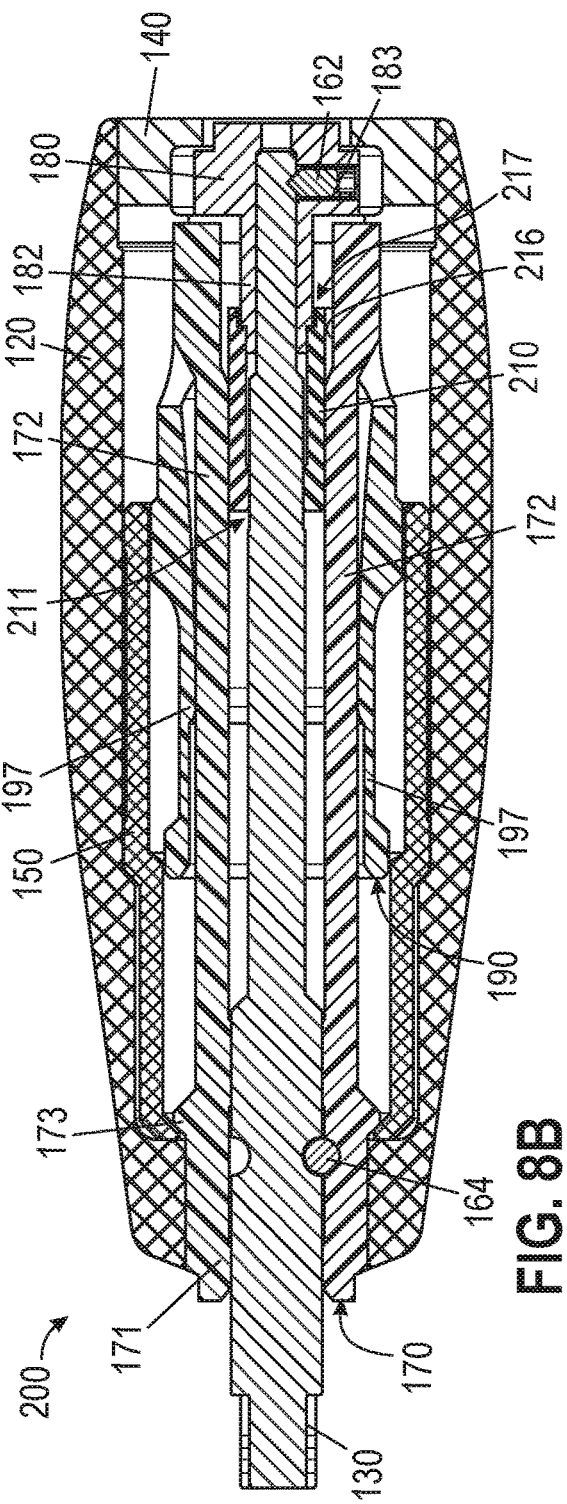

HEAD STABILIZATION DEVICE WITH DETACHABLE TORQUE APPLICATOR

PRIORITY

This application claims priority to U.S. Provisional Patent App. No. 62/939,053 entitled "Head Stabilization Device with Detachable Torque Applicator," filed Nov. 22, 2019, the disclosure of which is incorporated by reference herein.

BACKGROUND

The devices and methods disclosed pertain to patient stabilization, and in particular head and neck stabilization using stabilization devices known as head stabilization devices, which are also referred to as head fixation devices (hereinafter referred to as "HFDs" or "HFD" in singular). HFDs are sometimes used during a variety of surgical and other medical procedures, for example during head or neck surgery or testing where it would be desirable to securely hold a patient's head in a certain position. When stabilizing a patient's head, techniques include invasive and non-invasive setups. Invasive setups can use stabilizing features in the form of pins that contact the patient's head and in particular skull. Non-invasive setups can use stabilizing features in the form of pads or other structures that are configured to contact the patient's head but without penetrating the skin. HFDs used with invasive and non-invasive setups include structures or assemblies that are configured to retain and position one or more stabilizing features.

HFDs are also configured with the ability to adjust their size to accommodate patients having varying head size. When stabilizing a patient with an HFD, one or more stabilizing features can be tightened in a controlled manner to apply a desired amount of force to the patient's head to achieve acceptable stabilization. The devices and methods herein also pertain to adjusting this force applied by the one or more stabilizing features. While a variety of head stabilization devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 6A depicts a cross section view of the torque applicator of FIG. 1, taken along line 6-6 of FIG. 5, shown with the applicator at a first torque setting.

FIG. 6B depicts a cross section view of the torque applicator of FIG. 1, taken along line 6-6 of FIG. 5, shown with the applicator at a second torque setting.

FIG. 7 depicts another side view of the torque applicator of FIG. 1, the torque applicator being rotated about its longitudinal axis 90 degrees from the side view of FIG. 5.

FIG. 8A depicts a cross section view of the torque applicator of FIG. 1, taken along line 8-8 of FIG. 7, shown with the applicator at the first torque setting.

FIG. 8B depicts a cross section view of the torque applicator of FIG. 1, taken along line 8-8 of FIG. 7, shown with the applicator at the second torque setting.

Figure 1:
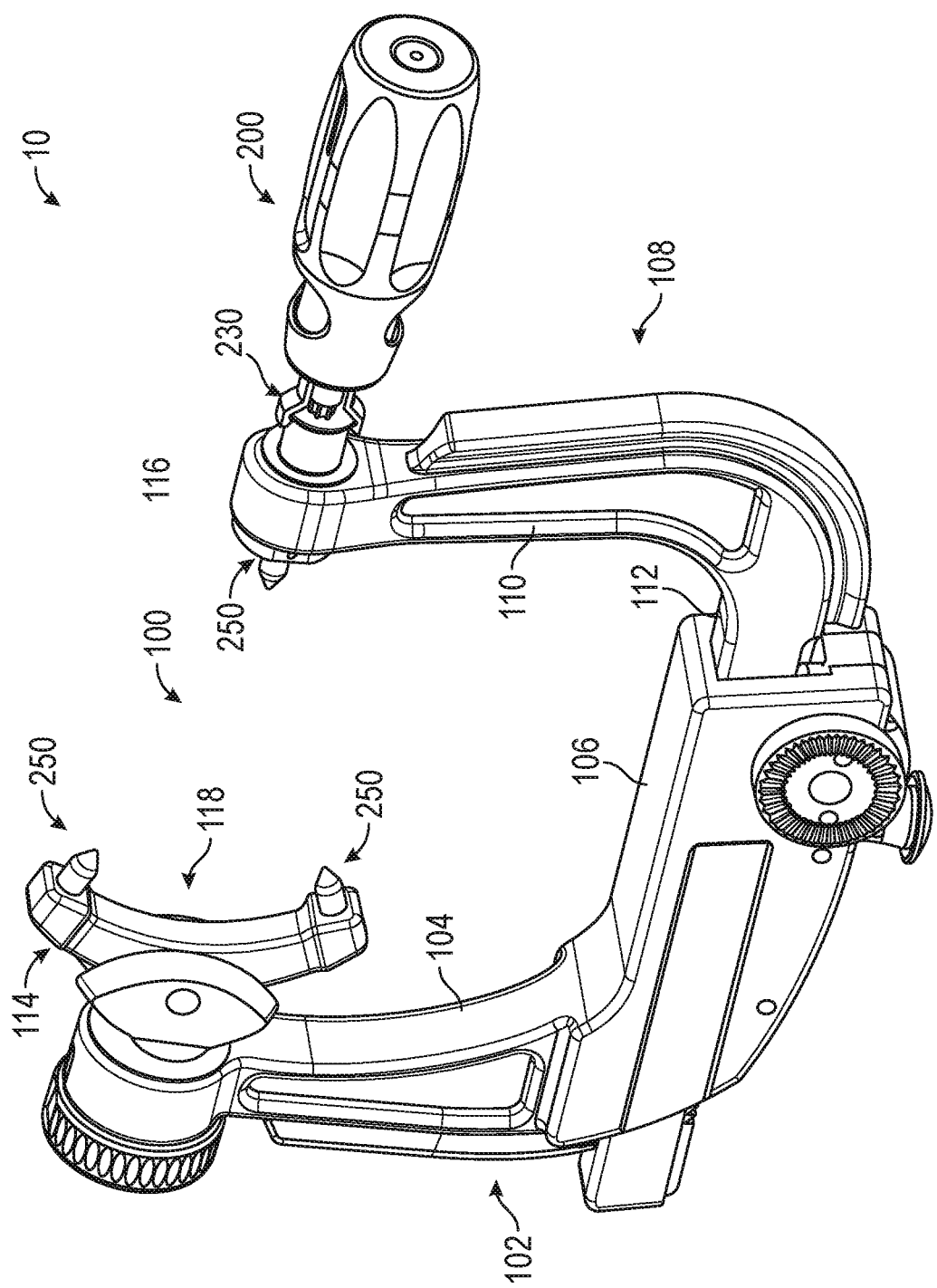
FIG. 1 depicts a perspective view of an exemplary patient head support system showing a skull clamp with a stabilization assembly having a detachable torque applicator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Patient Head Support System

Figure 2:
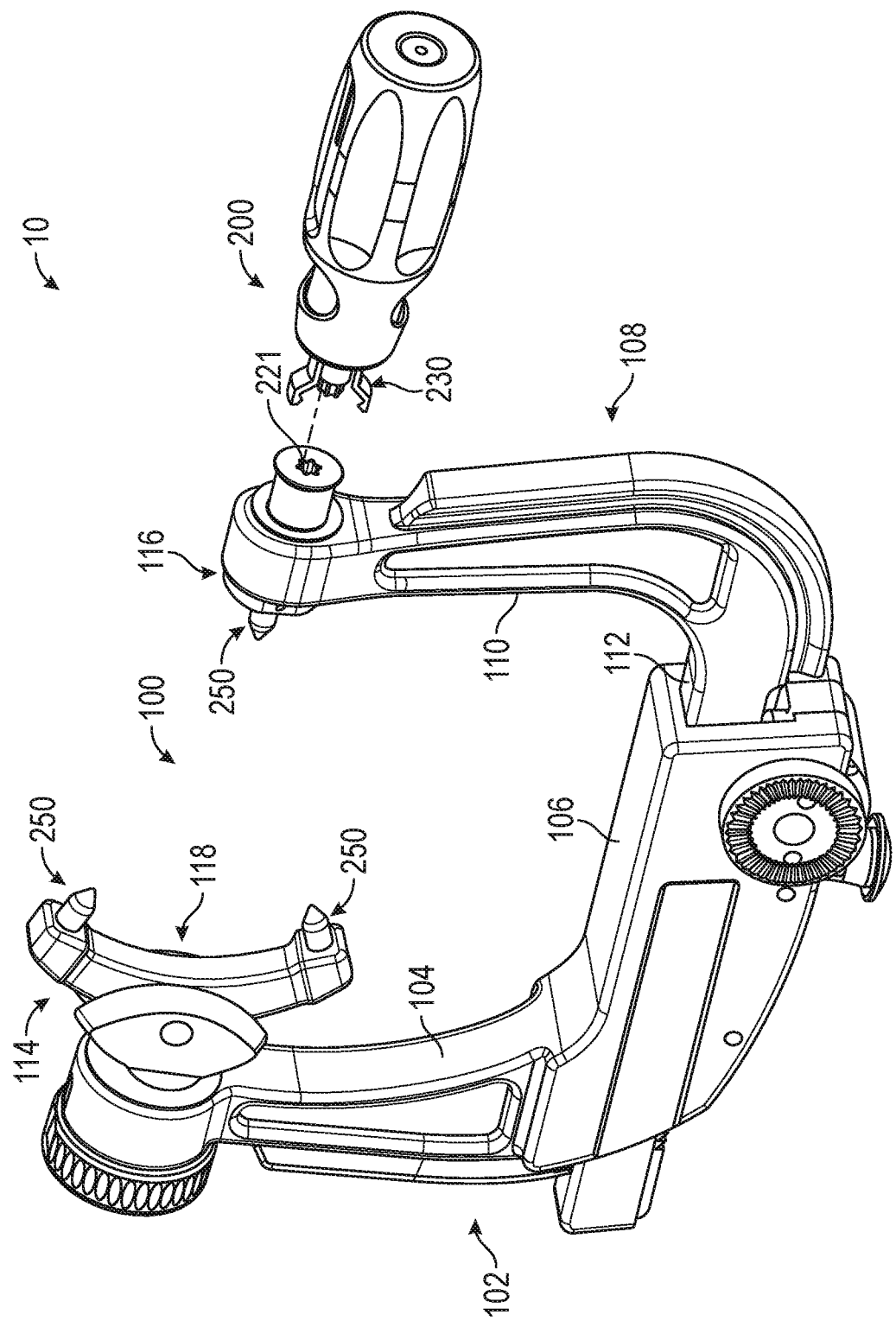
FIG. 2 depicts a perspective view of the patient head support system of FIG. 1, shown with the torque applicator detached from the stabilization assembly.

FIGS. 1 and 2 illustrate an exemplary patient head support system (10) having an HFD in the form of a skull clamp (100) and a torque applicator (200). Skull clamp (100)

includes an arm (102) defining an upright portion (104) and a lateral portion (106). Skull clamp (100) further includes an arm (108) defining an upright portion (110) and a lateral portion (112). As shown, lateral portions (106, 112) are configured to connect together in a selectively adjustable manner. This configuration permits changing the spacing between upright portions (104, 110) to accommodate patients having various head sizes.

Each upright portion (104, 110) of skull clamp (100) includes a bore at one end, with the bore configured to receive a stabilization assembly. In the present example, upright portion (104) is shown with stabilization assembly (114), while upright portion (110) is shown with stabilization assembly (116). Stabilization assembly (114) is configured with a rocker assembly (118) capable of holding two stabilization features (250). Stabilization assembly (116) is configured with a bore capable of holding a single stabilization feature (250). In one version, stabilization features (250) retained by stabilization assemblies (114, 116) are skull pins. However, in other versions stabilization features (250) retained by stabilization assemblies (114, 116) are pads or a combination of pins and pads. In this manner, system (10) can be in either an invasive or non-invasive configuration depending on the type or style of stabilizing features used.

Skull clamp (100) also includes torque applicator (200) that is configured to selectively connect with skull clamp (100) by way of stabilization assembly (116) and a coupling sleeve (230) of torque applicator (200). This selective connection is seen when comparing FIG. 1 and FIG. 2, where torque applicator (200) connects with skull clamp (100) in FIG. 1 and is detachable from skull clamp (100) as seen in FIG. 2. As will be shown and described below, torque applicator (200) includes coupling sleeve (230) (see also FIG. 12) that allows torque applicator (200) to securely and selectively connect with stabilization assembly (116) and remain connected without being held in position by a user. Coupling sleeve (230) can be actuated to remove or detach torque applicator (200) from stabilization assembly (116) of skull clamp (100). Again, further detail of the coupling sleeve will be provided below with reference to FIG. 12.

When in use, a patient's head is positioned within the space of head support system (10) between upright portions (104, 110) of skull clamp (100). Skull clamp (100) is then adjusted to bring upright portions (104, 110) of arms (102, 108) toward one another until stabilizing features (250) of stabilization assemblies (114, 116) nearly or just contact the head of the patient. Next, torque applicator (200) is used to adjust the amount of force that stabilizing features (250) apply to the head of the patient. This is accomplished by using torque applicator (200) to apply a predetermined amount of force to the head of the patient to achieve stabilization without applying excessive force that may cause trauma to the head of the patient. In this manner, torque applicator (200) includes features that prevent torque applicator (200) from applying more torque than the predetermined amount as set using torque applicator (200).

When applying torque, torque applicator (200) applies the predetermined force to stabilization feature (250) connected with stabilization assembly (116). Stabilization assembly (114) is generally opposite to stabilization assembly (116), and stabilization assembly (114) is fixed once its stabilizing features (250) contact the head of the patient. In this manner, an equal and opposite force is applied by opposing stabilization assemblies (114, 116). However, the number of stabilizing features (250), the position of each of stabilizing features (250), and the angle each stabilizing feature (250) makes with the head of the patient impacts the direction and magnitude of the applied stabilizing force. Thus, not all individual stabilizing features (250) necessarily apply the same magnitude or direction of force to the head of the patient. The sections that follow will describe further details concerning torque applicator (200) and its use.

II. Exemplary Detachable Torque Applicator with Rotatable Actuator

FIGS. 3-11 illustrate exemplary torque applicator (200). Torque applicator (200) is sometimes referred to herein simply as applicator (200). Referring to FIGS. 3-5, and 7, applicator (200) includes a housing (120). Housing (120) extends longitudinally from a proximal end of applicator (200) to a distal end of applicator (200). Housing (120) further generally defines an outer perimeter of applicator (200). At the distal end, housing (120) includes an opening (122) through which an elongated bit (130) extends. Applicator (200) defines a longitudinal axis (LA). Longitudinal axis (LA) defines a rotational axis about which elongated bit (130) and other components of applicator (200) may rotate. In the present example, distal end of elongated bit (130) has a six-point star shape; however, in other versions distal end of elongated bit (130) can have other shapes such as slotted, cross, square, among others that will be apparent to those of ordinary skill in the art in view of the teachings herein.

Figure 4:
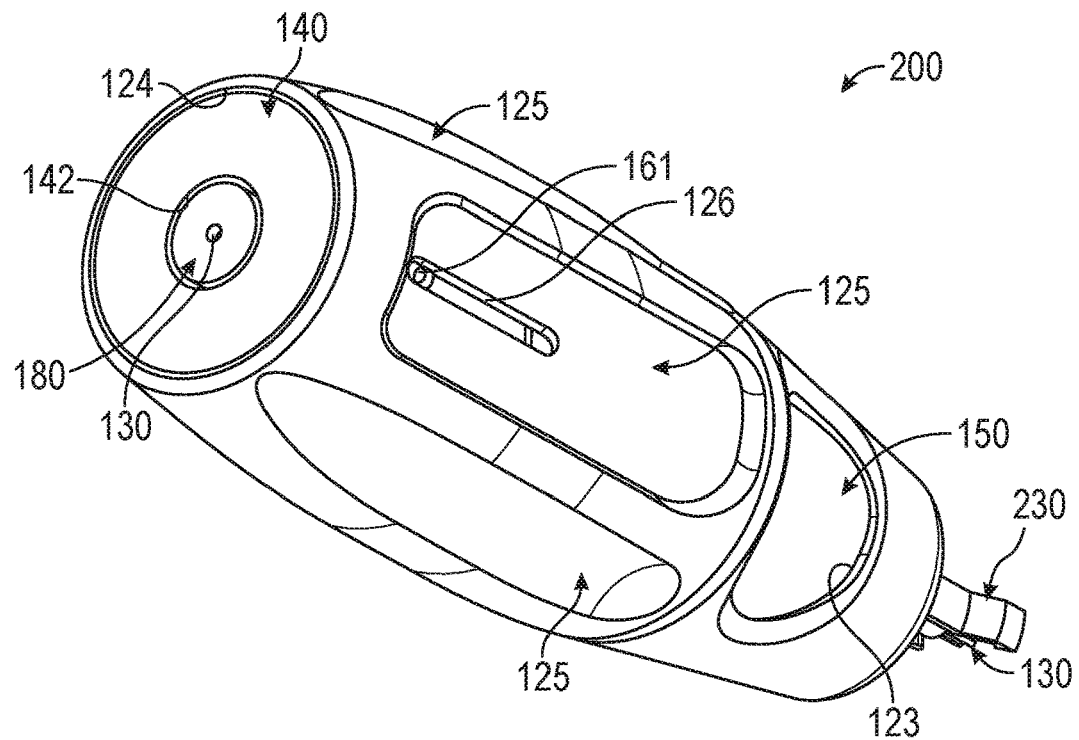
FIG. 4 depicts another perspective view of the torque applicator of FIG. 1.
Figure 5:
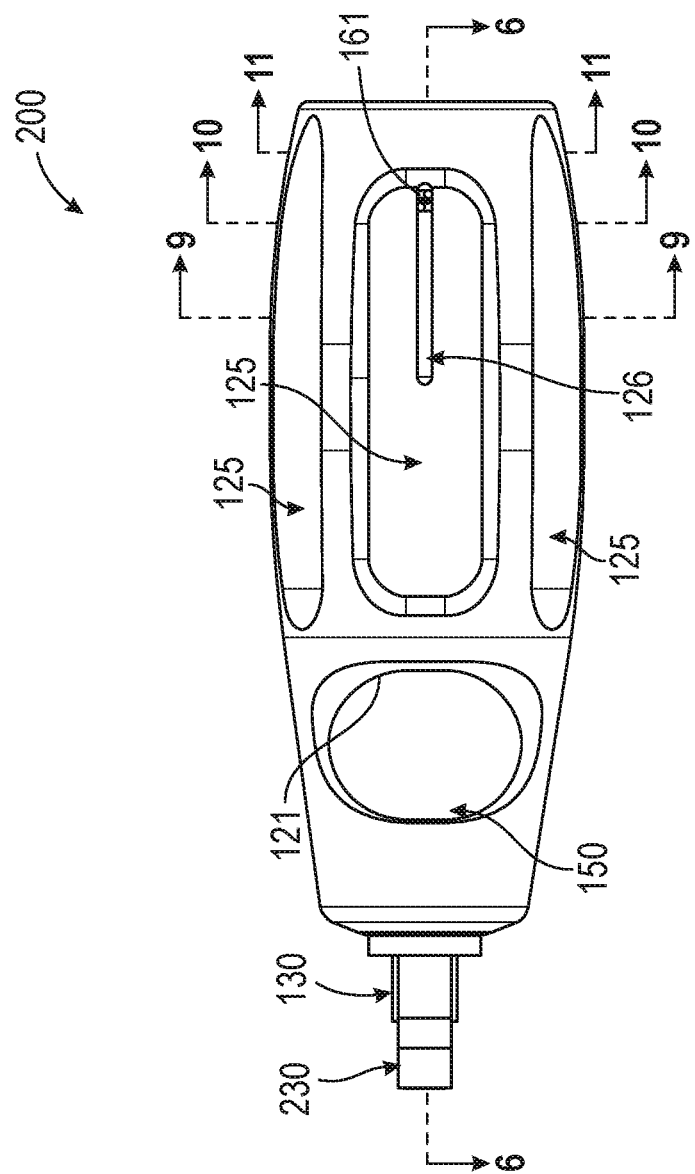
FIG. 5 depicts a side view of the torque applicator of FIG. 1.

At the proximal end of housing (120) as seen in FIG. 4, is another opening (124), and a cover (140) that fits within opening (124). In some versions cover (140) has a snap fit with housing (120), while in some other versions cover (140) can be secured to housing (120) by a pin that can extend through housing (120) and cover (140). In some versions, cover (140) includes a plurality of slots that provide visual access within housing (120). At a center of cover (140) is an opening (142) that is configured to receive a calibration sleeve (180), which is part of a calibration assembly or feature. As shown in FIG. 4, a proximal end of elongated bit (130) is received within calibration sleeve (180). In some versions, calibration sleeve (180) includes a pair of openings configured to receive a tool for rotating calibration sleeve (180) as will be described in further detail below when describing the calibration process.

Figure 3:
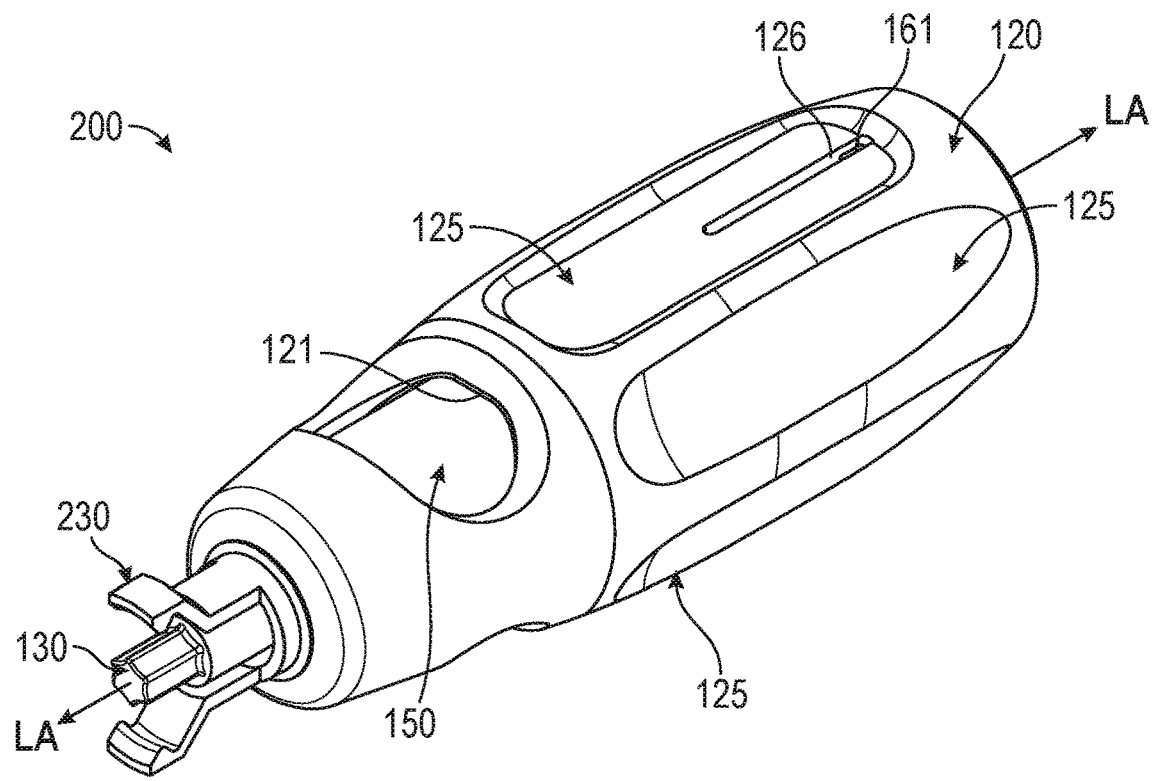
FIG. 3 depicts a perspective view of the torque applicator of FIG. 1.

Still referring to FIGS. 3 and 4, housing (120) also includes lateral openings (121, 123). Openings (121, 123) are located on opposing sides of housing (120). In the present example, openings (121, 123) are also generally located toward the distal end of housing (120). Openings (121, 123) provide access to an actuator (150), which can be used to adjust a torque setting for applicator (200) as will be described in greater detail below. Along an outer surface of housing (120) are elongated divots (125) that extend longitudinally. In the present example, divots (125) are spaced around the perimeter of housing (120). In this manner, divots (125) are configured as a grip feature to improve gripping ability when grasping torque applicator (200). In some versions, actuator (150) can include divots that extend longitudinally and that are spaced around the perimeter of actuator (150). In this manner, such divots can be configured as a grip feature to improve gripping ability when grasping actuator (150) to adjust the torque setting of applicator (200) by rotating actuator (150).

Two divots (125) of housing (120) include an elongated slot (126). In the present example, elongated slots (126) are on opposite sides of housing (120). Within each elongated slot (126) is a pin (161) configured to translate within its respective slot (126). As will be discussed in greater detail below, these pins (161) translate when actuator (150) is rotated to adjust a torque setting. In some versions, adjacent to elongated slots (126) is a scale of torque settings that are marked on the outer surface of housing (120). In such versions, pins (161) are force indicators by pointing to or associating with the scale. In some versions, the scale can be numeric, while in other versions, the scale can provide relative indication. By way of example only, and not limitation, a relative indication can include a color-coded graphic where one color may indicate an acceptable torque setting while another color or colors may indicate either too low or too high torque settings. In view of the teachings herein, other ways to provide feedback or indication of a torque setting will be apparent to those of ordinary skill in the art.

In some versions, along the perimeter of housing (120) near the proximal end can be a plurality of bores that extend laterally into housing (120) and are spaced evenly around the perimeter of housing (120). Such bores can be configured to receive a set screw (162) (see FIGS. 8A and 8B). As will be described in greater detail below, set screw (162) is configured to secure a calibration setting for torque applicator (200). In some versions there can also be an additional bore that can be configured to receive a pin to secure cover (140) with housing (120) as mentioned above.

In some versions, at or near the distal end of housing (120) can be a lateral bore configured to receive a pin configured to secure a fork member (170) (see FIGS. 6A and 6B) with housing (120). Fork member (170) is a control feature for changing the torque applied by applicator (200) as will be described in greater detail below. With this exemplary pinned connection with housing (120), fork member (170) rotates in unison with housing (120) as will also be further described below. In some other versions, such a pinned connection could be replaced by another fastener type such as a grub screw.

Referring to FIGS. 5-11, further details of internal components of torque applicator (200) will be described along with operational features of torque applicator (200). Beginning with FIGS. 5-6B, actuator (150) is shown as a tubular structure with an interior space (153) and having a distal opening (154) and a proximal opening (155). Positioned within interior space (153) and extending from proximal end (155) of actuator (150) is sleeve (190). Sleeve (190) is also shown as a tubular structure with an interior space (192) and having a distal opening (193) and a proximal opening (194).

Actuator (150) includes a threaded portion (152) that threadably engages with a threaded portion (191) of sleeve (190). In this manner, rotation of actuator (150) causes translations of sleeve (190) because of the threaded engagement between these components. The direction of the translation of sleeve (190) depends on the direction of rotation of actuator (150). In the present version, rotation of actuator (150) in a clockwise manner when viewing applicator (200) from a proximal end causes sleeve (190) to translate proximally as seen in FIG. 6B when compared to FIG. 6A. In an opposite manner, rotation of actuator (150) in a counter-clockwise manner when viewing applicator (200) from a proximal end causes sleeve (190) to translate distally. In the present example, sleeve (190) is configured to translate over a distance that spans from cover (140) at one end of applicator (200), to lip (173) of fork member (170) at the other end of applicator (200). In other versions, actuator (150) and sleeve (190) can be configured to cause translation of sleeve (190) in a manner opposite to what is described immediately above, or to a lesser extent in terms of translation distance, as will be apparent to those of ordinary skill in the art in view of the teachings herein. Further, actuator (150) can be having various structure and forms besides the rotating tubular structure illustrated in FIGS. 5-11. For instance, actuator (150) can be structured as a thumbwheel, a rotating sleeve or tubular body, a slider configured to translate, among other structural forms that will be apparent to those of ordinary skill in the art in view of the teachings herein.

Sleeve (190) includes pins (161) at its proximal end as mentioned above. As sleeve (190) translates based on rotation of actuator (150), pins (161) move with sleeve (190) along slots (126) of housing (120). As mentioned above, pins (161) are configured in this manner to act as a force indicator by indicating a torque setting as will be understood more clearly from the description below. Because pins (161) extend within slots (126) of housing (120), rotation of housing (120) will cause corresponding rotation of pins (161) and thus sleeve (190) and connected actuator (150). This rotation of actuator (150) and sleeve (190) with housing (120) occurs without altering the relative positions of sleeve (190) with respect to actuator (150).

Sleeve (190) is also configured with a lateral opening (196) within its sidewall. Openings (196) are configured to reduce mass and also to provide access to interior space (192) for cleaning, observation, etc. In some versions the number of lateral openings (196) can be greater or fewer than that illustrated in the present example. Sleeve (190) includes an inner surface (198) defining interior space (192). Inner surface (198) generally tapers from a proximal end to a distal end of sleeve (190), however a portion (197) of sleeve (190) is straight or non-tapered.

Fork member (170) extends through interior space (153) of actuator (150) and extends from distal opening (154). Fork member (170) includes a distal body portion (171) and a pair of arms (172) extending proximally from body portion (171). Body portion (171) includes a lip (173). When assembled with actuator (150), lip (173) has a diameter larger than distal opening (154) of actuator (150) such that fork member (170) cannot pass through distal opening (154) of actuator (150). In some other versions, fork member (170) may also be pinned with housing (120) by a pin. In this manner, actuator (150) is maintained in its longitudinal position relative to housing (120) because actuator (150) cannot move proximally past lip (173) of fork member (170). Similarly, distal end of actuator (150) abuts or is immediately adjacent to an inner distal flange (129) of housing (120), which prevents actuator (150) from moving distally relative to housing (120).

As shown in FIGS. 8A and 8B, elongated bit (130) extends through body portion (171) of fork member (170), and ultimately emerges from a distal end of housing (120). Elongated bit (130) and body portion (171) of fork member (170) are configured such that fork member (170) and elongated bit (130) can rotate independent of one another. As described further below, such independent rotation occurs when a torque setting or limit is reached and elongated bit (130) does not rotate with further housing (120) rotation although fork member (170) does. Still, under certain conditions elongated bit (130) and fork member (170) can rotate in unison. As also described below, this could be the case when a torque setting or limit is not yet reached and elongated bit (130) rotates in unison with fork member (170). In the present example, applicator (200) includes a pin (164) that is located between body portion (171) of fork member (170) and elongated bit (130). Pin (164) is configured to permit rotation between elongated bit (130) and fork member (170) based on the conditions during use of applicator (200). In some versions, more than one pin (164) may be used between bit (130) and fork member (170).

Referring to FIGS. 7, 8A, and 8B, the interaction between sleeve (190) and fork member (170) will be described to explain setting a predetermined or prescribed amount of torque. As mentioned above, fork member (170) includes pair of arms (172) that extend proximally from body portion (171). At a proximal end, arms (172) are configured to selectively contact a knob (210). When the proximal end of arms (172) contact knob (210) under certain conditions, arms (172) bend or deflect away from longitudinal axis (LA) in response to such contact. Based on this contact between arms (172) and knob (210) under these conditions, a bending stress is imparted to arms (172). In at least some examples, this bending stress occurs when a force is exerted generally on arms (172) where the direction of the force is not parallel with a longitudinal axis or length of the arms (172). In some but not all instances, the direction of the force may be orthogonal to a longitudinal axis or length of the arms (172). The result of such force is a bending or deflecting of arms (172) from their neutral position or state. However, proximal ends of arms (172) can contact knob (210) under other conditions where arms (172) do not bend or deflect away from longitudinal axis (LA).

Figure 9:
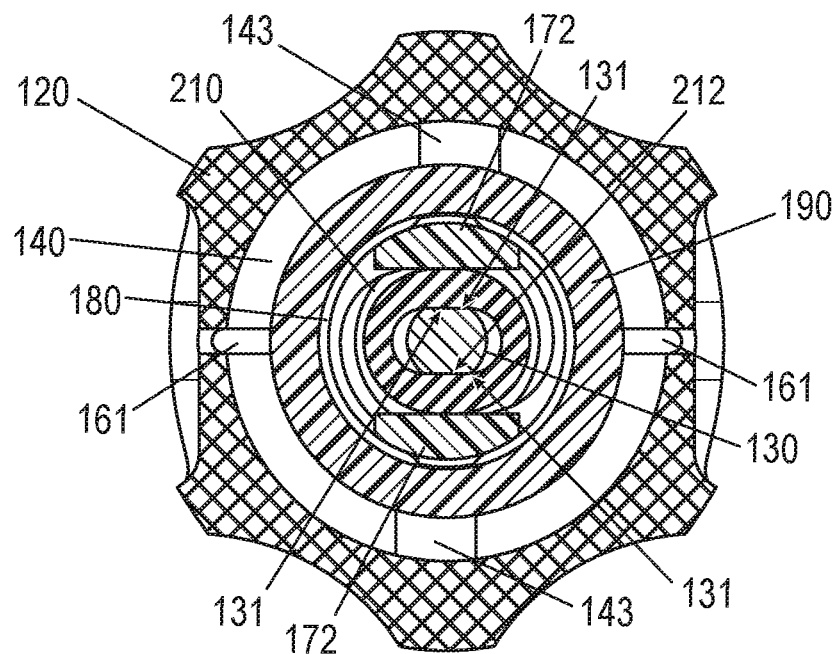
FIG. 9 depicts a cross section view of the torque applicator of FIG. 1, taken along line 9-9 of FIG. 5.

Referring to FIGS. 8 and 9, knob (210) is positioned about elongated bit (130) such that bit (130) extends through knob (210). Moreover, knob (210) includes a distal opening (211) with flat sides (212). Elongated bit (130) includes a profile with flat sides (131) along its length at the position where elongated bit (130) passes through opening (211). The corresponding flat sides (131, 212) of bit (130) and opening (211) of knob (210) create an interference fit between elongated bit (130) and knob (210). This interference fit causes knob (210) and elongated bit (130) to rotate in unison. Thus, when knob (210) rotates, a corresponding rotation of elongated bit (130) occurs.

Figure 10A:
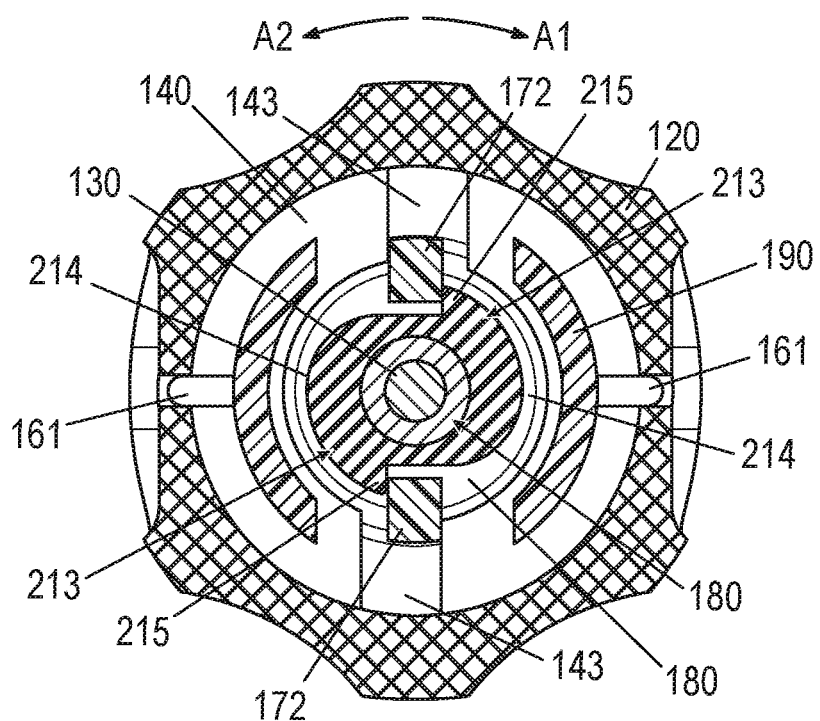
FIGS. 10A-10C depict series views in cross section, of the torque applicator of FIG. 1, taken along line 10-10 of FIG. 5, showing positions of components of the torque applicator in use.
Figure 10B:
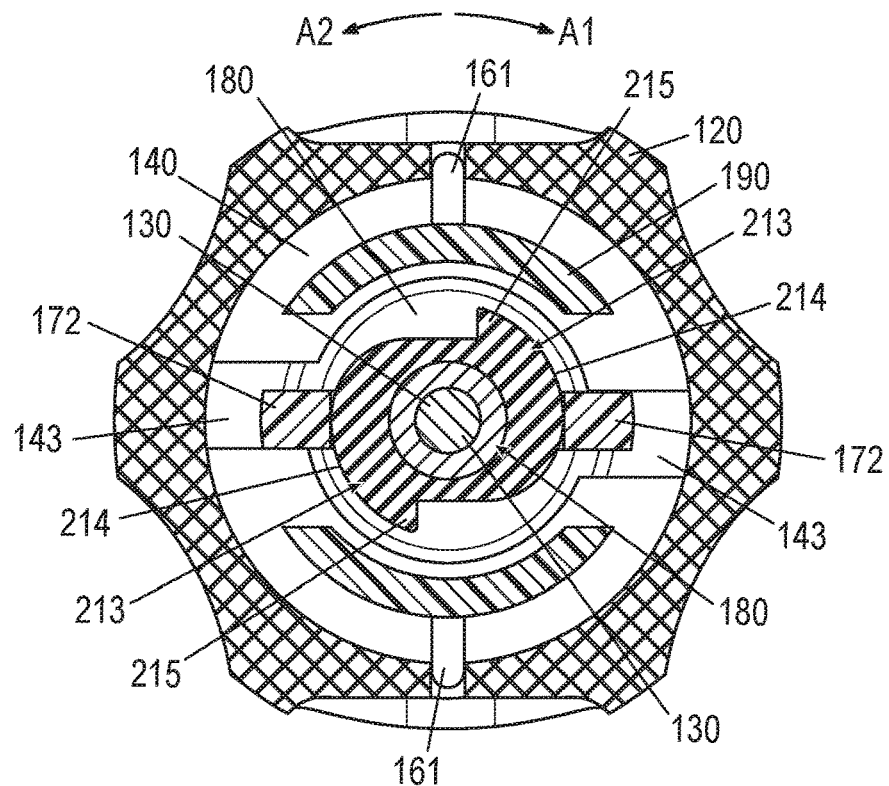
Figure 10C:
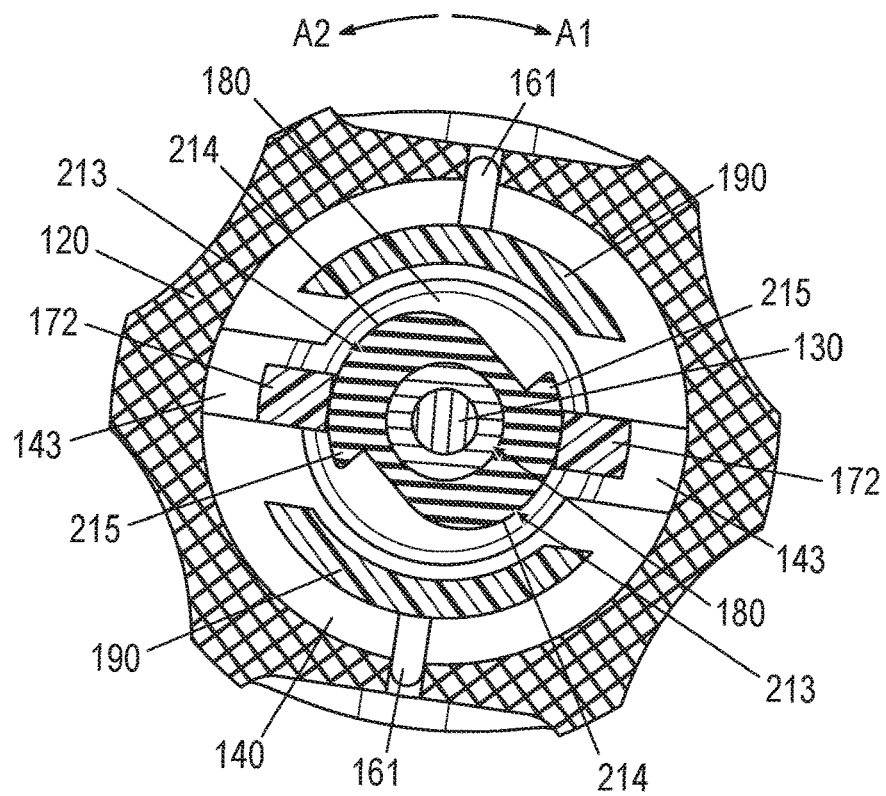

Referring to FIGS. 10A-10C, knob (210) includes a pair of curved hook features (213). As shown, proximal end of arms (172) is configured to contact respective hook features (213) when fork member (170) is rotated counterclockwise when viewing applicator (200) from its proximal end. This is shown in FIG. 10A by an arrow (A1) showing the direction of rotation. In this fashion, rotation of fork member (170) counterclockwise will cause corresponding rotation of knob (210) and elongated bit (130) counterclockwise. Moreover, the contact between arms (172) and hook features (213) of knob (210) in this manner occurs without causing bending or deflection of arms (172) away from longitudinal axis (LA). Also, proximal ends of arms (172) are received within respective slots (143) of cover (140). Slots (143) maintain the position of arms (172) such that arms (172) do not deflect, i.e., when proximal ends of arms (172) contact hook features (213) of knob (210). As mentioned earlier, fork member (170) can be secured to housing (120) by a pin or other structure such that fork member (170) rotates in unison with housing (120). Consequently, rotation of housing (120) counterclockwise when viewing applicator (200) from its proximal end produces a corresponding rotation of elongated bit (130) in the same direction. This counterclockwise rotation can be considered one condition of use of torque applicator (200). In at least some instances, rotation in this manner loosens or reduces the contact or engagement of stabilizing feature (250) of stabilizing assembly (116) with the head of the patient.

Now considering rotation of housing (120) clockwise when viewed from the proximal end, fork member (170) will rotate in unison with housing (120) for the reasons mentioned above. Referring to FIGS. 10A-10C, this clockwise rotation causes arms (172) to move in the same manner, which is shown by the direction of an arrow (A2). The distance between arms (172) is smaller than the diameter of knob (210) across hook features (213) at its largest point. Consequently, as arms (172) rotate in the direction of arrow (A2), proximal ends of arms (172) will contact or engage with an outer curved surface (214) of hook features (213). Furthermore, because the distance between the proximal ends of arms (172) is smaller than the largest diameter point of hook features (213), the contact of the proximal ends of arms (172) with outer curved surface (214) of hook features (213) causes arms (172) to adopt a bent or deflected position or state as shown in FIGS. 10B and 10C. As shown in FIGS. 9-10C, slots (143) of cover (140) are elongated to allow deflection of proximal ends of arms (172) away from longitudinal axis (LA) when applicator (200) is in use in this manner.

With this bent or deflected configuration for arms (172), arms (172) exert an inward directed force onto hook features (213) of knob (210). This creates a holding or squeezing affect where arms (172) hold or squeeze knob (210). When the force applied by arms (172) is higher than the resistance force applied to elongated bit (130)—based on its engagement with stabilizing assembly (116) and stabilizing feature's (250) contact with the head of the patient—then rotation of housing (120) and arms (172) of fork member (170) permit arms (172) to hold knob (210) with enough force to rotate knob (210) and connected elongated bit (130) in unison with arms (172). In this manner, stabilizing feature (250) of stabilizing assembly (116) can be tightened by rotating housing (120) clockwise when viewed from the proximal end of applicator (200).

When the resistance force applied to elongated bit (130)—based on its engagement with stabilizing assembly (116) and stabilizing feature's (250) contact with the head of the patient—is higher than the force arms (172) are applying to knob (210), then arms (172) will slide or slip past hook features (213) of knob (210). When arms (172) slide or slip enough, they reach the position as shown in FIG. 10A by arms (172) resiliently snapping back or returning to their relaxed state. In this neutral or relaxed state, arms (172) are no longer bent or deflected outward from longitudinal axis (LA). Thus arms (172) and connected housing (120) will have rotated, but without corresponding rotation of knob (210) and elongated bit (130). So, although further tightening or rotational force may have been applied to housing (120) and fork member (170), such further tightening or rotational force is not transferred to knob (210) and elongated bit (130) and thus stabilizing assembly (116) to which elongated bit (130) is connected with is also not subject to the further tightening or rotational force. This clockwise rotation where knob (210) rotates can be considered another condition of use of torque applicator (200), and similarly clockwise rotation where knob (210) does not rotate can be considered another condition of use of torque applicator (200).

In the present example of torque applicator (200), the amount of force exerted or applied on knob (210) by arms (172) is a function of a bending length of arms (172). For instance, referring to FIGS. 8A and 8B, arms (172) are shown having different bending lengths. Furthermore, applicator (200) is configured such that the bending length of arms (172) is adjustable. This adjustment is accomplished by the interaction between sleeve (190) and arms (172) of fork member (170).

Sleeve (190) includes a portion (197) that is positioned alongside arms (172). As shown when comparing FIGS. 8A and 8B, portion (197) is further distally located in FIG. 8A compared to FIG. 8B. The bending length can be defined as the length of arms (172) that extend proximally from portion (197) of sleeve (190) to the point where arms (172) are alongside a distal portion of knob (210). Accordingly, FIG. 8A illustrates a condition with a first bending length that is greater than a second bending length of another condition shown in FIG. 8B. As mentioned above, rotation of actuator (150) causes translation of sleeve (190), which in turn provides the different bending lengths for arms (172). Thus, the bending length of arms (172) of fork member (170) are controlled by rotation of actuator (150). As will be described further below, the bending length of arms (172) is also impacted by calibration steps where a distal portion of knob (210) is moved relative to arms (172). However, calibration in this manner is configured as a separate calibrating process, and is not configured to replace, or take the place of, adjusting the bending length to control torque in use.

As it pertains to torque settings, a smaller bending length is associated with a greater bending force. In other words, as the bending length of arms (172) becomes shorter, more force is required to bend arms (172). Similarly, the greater the force would be that is applied to hook features (213) by arms (172). Accordingly, in the present version the shortest bending length of arms (172), and thus the greatest torque setting, would be when sleeve (190) is translated to its most proximal position. Likewise, the longest bending length of arms (172), and thus the least torque setting, would be when sleeve (190) is translated to its most distal position.

In the present version, the bending force is applied based on the interaction between knob (210) and arms (172). More specifically, the interaction here is between hook features (213) of knob (210) and arms (172). For example, with a shorter or smaller bending length of arms (172), based on the position of sleeve (190), greater force will be required to cause bending of arms (172) to the point where arms (172) slide or slip past hook features (213) of knob (210) when housing (120) is rotated clockwise. In other words, applicator (200) can apply a greater torque to stabilizing assembly (116) when tightening. In the opposite manner, the longer or greater the bending length of arms (172), again based on the position of sleeve (190), less force will be required to cause bending of arms (172) to the point where arms (172) slide or slip past hook features (213) of knob (210) when housing (120) is rotated clockwise. In other words, applicator (200) applies less torque to stabilizing assembly (116) when tightening.

By way of example only, and not limitation, in one exemplary use applicator (200) may be adjusted by rotation of actuator (150) such that the torque indicator reads 60 newton meters. Head support system (10) is configured with a patient's head positioned within skull clamp (100), and with skull clamp (100) having stabilization assemblies (114, 116) configured with skull pins as stabilizing features (250). Skull clamp (100) is adjusted to move arms (102, 108) so that skull pins contact the head of the patient. Applicator (200) connects with stabilizing assembly (116), with elongated bit (130) engaged with a star-shaped recess (221) of stabilizing assembly (116). Housing (120) of applicator is then rotated in a clockwise manner when viewed from its proximal end. The rotation of housing (120) causes corresponding rotation of fork member (170), and cover (140) as described above. Arms (172) of fork member (170) rotate around knob (210) and ultimately contact outer curved surfaces (214) of hook features (213), for example as shown in FIG. 10B.

Because stabilizing feature (250) of stabilization assembly (116) has not yet been tightened, it requires less than 60 newton meters of force to tighten them. Consequently, rotating housing (120) of applicator will tighten the skull pin stabilizing feature (250) connected with stabilizing assembly (116). This occurs because the proximal ends of arms (172) engage or contact hook features (213) of knob and apply sufficient force on knob (210) to hold and rotate knob (210) and elongated bit (130) extending therethrough. FIG. 10C shows a view where knob (210) and elongated bit (130) have been rotated based on the force arms (172) apply to hook features (213) of knob (210) as mentioned.

After some tightening, stabilizing feature (250) of stabilizing assembly (116) requires a force greater than 60 newton meters for further tightening. At this point, rotation of housing (120) further clockwise again causes arms (172) of fork member (170) to rotate. However, the force required to bend arms (172) away from longitudinal axis (LA) to the point where arms (172) will slide or slip along outer curved surfaces (214) of hook features (213) is set at 60 newton meters. As mentioned, a torque setting on applicator (200) greater than 60 newton meters is needed to further tighten stabilizing feature (250). Since in this example the torque setting is at 60 newton meters, rotating housing (120) will cause arms (172) to now slide or slip past hook feature (213). By way of example, this is illustrated in the series views when arms (172) as shown in FIG. 10C, for example, would slide past hook features (213) and adopt the position shown in FIG. 10A, for example. When this occurs, arms (172) will snap or click back into the position shown in FIG. 10A as arms (172) clear hook features (213) such that the bending or deflection force on arms (172) is removed. This snap or click provides a feedback feature of applicator (200) that signals to a user that the torque limit has been reached when tightening stabilization feature (250). With this action, knob (210) and elongated bit (130) do not rotate with the rotation of housing (120) and fork member (170) under these conditions.

If a user of patient head support system (10) decided that greater clamping pressure was desired, the torque setting could be increased by rotation of actuator (150), for example to 100 newton meters. Thereafter, further rotation of housing (120) of applicator (200) will rotate arms (172) such that proximal ends of arms (172) contact outer curved surface (214) of hook features (213) and will bind against hook features (213) of knob (210) with enough force to cause rotation of knob (210) and elongated bit (130) extending therethrough. Once stabilizing feature (250) of stabilizing assembly (116) is tightened to the point where it requires a force greater than 100 newton meters to further tighten stabilizing feature (250), then rotation of housing (120) of applicator (200) will again rotate arms (172), but elongated bit (130) and knob (210) will apply enough bending force to arms (172) that arms (172) will bend and slide or slip past hook features (213) of knob (210) instead of gripping and rotating knob (210).

When the time comes to loosen the stabilizing feature, and possibly remove the patient's head from skull clamp (100), applicator (200) is engaged with recess (221) and applicator (200) is rotated counterclockwise when looking from the proximal end of applicator (200). With the configuration of arms (172) and knob (210), no torque setting adjustment with actuator (150) and sleeve (190) is needed before loosening the stabilizing feature. As mentioned above, with the counterclockwise rotation, proximal ends of arms (172) contact a tip region (215) of hook features (213) and thereby rotate knob (210) and elongated bit (130) irrespective of the bending length configuration of arms (172) in conjunction with sleeve (190). The above descried example is merely exemplary. In view of the teachings herein, those of ordinary skill in the art will appreciate other ways to use the devices and systems shown and described herein to securely stabilizing the head of a patient at a known clamping force without exceeding the desired clamping force.

In addition to the bending forces on arms (172) described above, and the impact arms (172) have on gripping or applying force to knob (210) to either rotate knob (210) or slip past features of knob (210), frictional forces also influence applicator's (200) torque setting and application. For instance, frictional forces exist where proximal ends of arms (172) contact hook features (213) of knob (210). Thus, the threshold at the torque limit where the arms (172) slide or slip along and past hook features (213) is a function of the bending force applied to arms (172) and the frictional force between arms (172) and hook features (213) of knob (210). In some instances, the materials of construction of arms (172) and/or knob (210) can be configured or modified to provide greater or lesser friction between these components. In view of the teachings herein, other ways to control and modify the interaction of forces between arms (172) and hook features (213) of knob (210) will be apparent to those of ordinary skill in the art.

FIGS. 6A, 6B, 8A, 8B, and 11 illustrate features of applicator (200) configured to calibrate applicator (200) with respect to its torque setting capability. As shown, applicator (200) includes calibration sleeve (180). As mentioned above, calibration sleeve (180) is located at the proximal end of applicator (200). Calibration sleeve (180) is position within an opening of cover (140) and extends distally within housing (120) of applicator (200). In some versions, a proximal portion of calibration sleeve (180) can include a pair of openings configured to receive a tool for rotating and thereby adjusting calibration sleeve (180). In other versions, calibration sleeve (180) is rotatable by hand or other tools when cover (140) and/or housing (120) are disassembled from applicator (200) thereby providing access to calibration sleeve (180) for adjustment. A distal portion of calibration sleeve (180) includes a threaded portion (182).

Threaded portion (182) of calibration sleeve (180) engages with a threaded portion (216) of knob (210). As shown in FIGS. 6A, 6B, 8A, and 8B, knob (210) includes an opening (217) extending through knob (210) from its proximal end to its distal end. Threaded portion (216) is located along an inner surface of opening (217). Furthermore, the distal portion of calibration sleeve (180) is configured to fit within opening (217) of knob (210) with threaded portions (182, 216) threadably engaging. In this manner, when calibration sleeve (180) is rotated, knob (210) translates distally or proximally depending on the direction of rotation of calibration sleeve (180).

As seen best in FIGS. 8A and 8B, a distal portion of knob (210) is positioned along an inner surface of arms (172) of fork member (170). Translation of knob (210), based on rotation of calibrating sleeve (180), causes the distal portion of knob (210) to move along the inner surface of arms (172). Based on the amount the distal portion of knob (210) overlaps the inner surface of arms (172), the bending length of arms (172) is adjustable. Controlling the bending length in this respect provides for a way to calibrate the torque setting.

Figure 11:
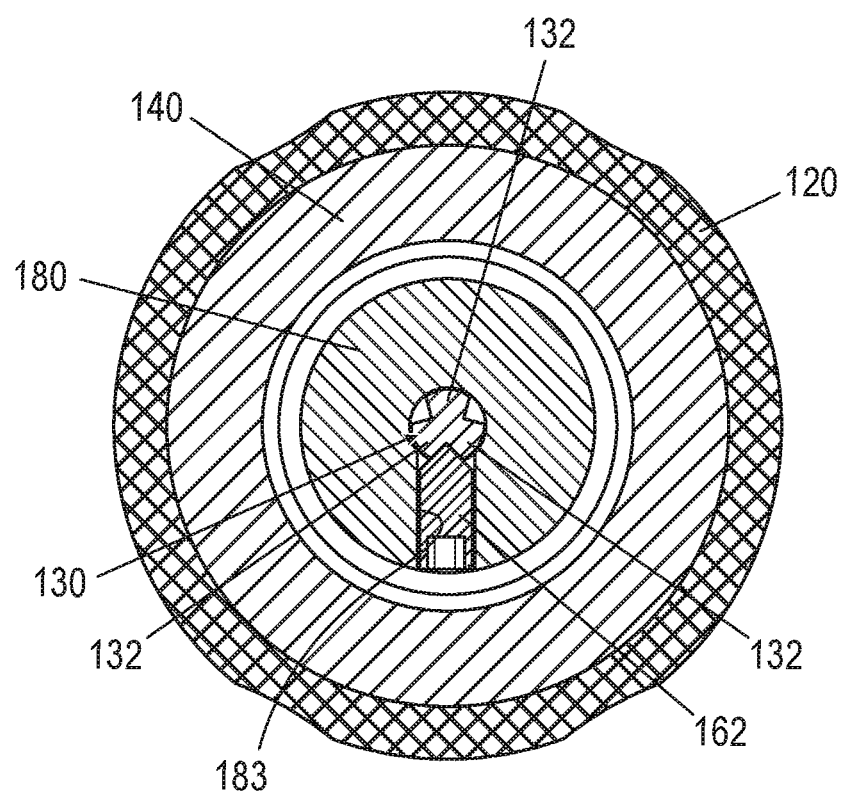
FIG. 11 depicts a cross section view of the torque applicator of FIG. 1, taken along line 11-11 of FIG. 5.

In an exemplary calibration sequence, a first step is to remove cover (140) and then set screw (162) from the proximal end of applicator (200). As shown in FIG. 11, set screw (162) is configured to connect calibration sleeve (180) with elongated bit (130). Elongated bit (130) includes a spoke-shaped profile along this location as shown. When set screw (162) is installed, a tip of the set screw is received in the space between two spokes (132) of spoke-shaped profile of elongated bit (130). By removing set screw (162), calibration sleeve (180) can then be rotated. As mentioned above, this rotation of calibration sleeve (180) causes corresponding translation of knob (210) based on its threaded engagement with calibration sleeve (180). In this respect, set screw (162) is removed from contact with elongated bit (130) so that knob (210) can translate in response to rotation of calibration sleeve (180). As mentioned above, the arrangement of flat sides (131, 212) of elongated bit (130) and knob (210) shown in FIG. 9, provide that with set screw (162) engaged with elongated bit (130), rotation of calibration sleeve (180) would cause rotation of elongated bit (130), which would cause corresponding rotation of knob (210). Accordingly, set screw (162) is removed from elongated bit (130) such that elongated bit (130) remains stationary when rotating calibration sleeve (180) to translate knob (210) for calibration.

During calibration steps, applicator (200) can be checked against a reference device with a known torque or used with a torque measurement device. For instance, if connected with a torque measurement device or used with a reference device with a known torque of 80 newton meters, applicator (200) can be adjusted by rotation of actuator (150) such that pins (161) indicate a torque setting of 80 newton meters. Applicator (200) can then be used with the torque measurement device or reference device with the known torque of 80 newton meters to see if applicator is providing the torque setpoint of 80 newton meters. If the actual torque provided by applicator (200) is lower or higher compared to the 80 newton meter setting, then calibration sleeve (180) can be adjusted so that knob (210) is translated to provide for adjustment of the torque output of applicator (200) to achieve 80 newton meters in this example.

Once calibration is complete such that applicator (200) is providing torque output matching the setpoint of the torque, then set screw (162) is fully inserted to fix or secure the relative position of knob (210), calibration sleeve (180), and elongated bit (130). In some other versions, applicator (200) includes a plurality of bores that extend lateral from housing (120) toward longitudinal axis (LA). In one such version there may be six such bores evenly spaced around the perimeter of applicator (200). In this such version, when inserting set screw (162) after calibration, a threaded bore (183) of calibration sleeve (180) is aligned with one of the bores and set screw (162) can then be inserted and secured within the bore and to threaded bore (183). In one such example with these bores in housing (120) there may be six such bores, and applicator (200) provides for calibration in at least six increments, or every 60 degrees about applicator's (200) circumference. In other versions, applicator (200) may have greater or fewer of such bores for receiving set screw (162) for calibration, thus differing increments of calibration. In the present illustrated example without such bores, the calibration increments are dictated by the number of spaces between spokes (132) of elongated bit (130). For instance, with a three spoke configuration, calibration can be done in three increments, or every 120 degrees about applicator's circumference. The above torque calibration structures and steps are exemplary. In view of the teachings herein, other structures and techniques for calibrating a torque setting of applicator (200) will be apparent to those of ordinary skill in the art.

Figure 12:
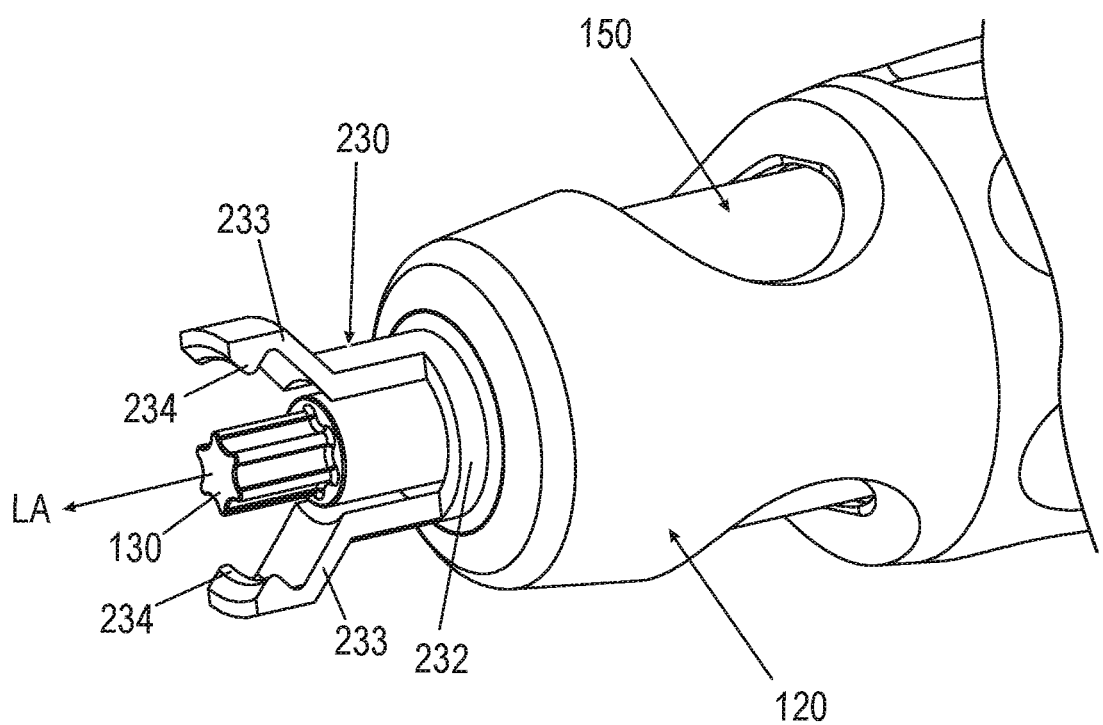
FIG. 12 depicts a partial perspective view of an exemplary coupling sleeve of the torque applicator of FIG. 1.
Figure 13:
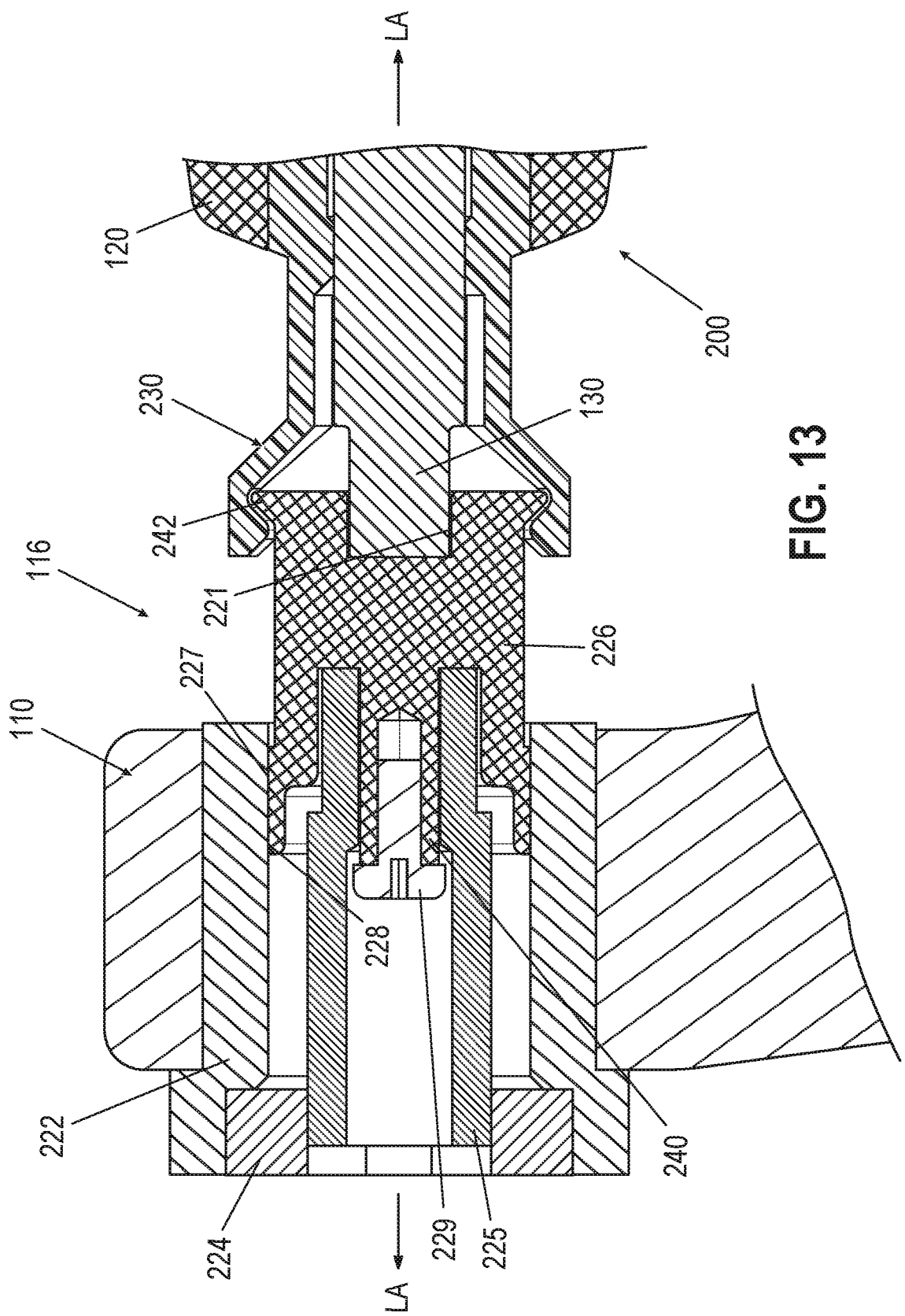
FIG. 13 depicts a cross section view of portions of the stabilization assembly of the skull clamp of FIG. 1, showing the coupling sleeve connection with the stabilization assembly.

FIGS. 12 and 13 depict closer views of coupling sleeve (230) that is useable with applicator (200). Coupling sleeve (230) is configured to connect with applicator (200) and further selectively connects with stabilization assembly (116). In the present example, coupling sleeve (230) is an extension of fork member (170) that extends distally from housing (120) of applicator (200). In other versions, coupling sleeve (230) may be separate from fork member (170) and may connect with applicator (200) in other ways that will be apparent to those of ordinary skill in the art in view of the teachings herein. With these connections, applicator (200) is selectively connectable and detachable from stabilization assembly (116) of skull clamp (100).

Coupling sleeve (230) includes a collar (232) and a pair of attachment features (233) that connect with collar (232) and extend distally therefrom. Attachment features (233) are configured as elongated angled bodies with latch members (234) that are oriented inward toward longitudinal axis (LA). Attachment features (233) are further configured as resilient members such that attachment features (233) are deflectable either toward or away from longitudinal axis (LA) depending on the direction from which a force is applied on attachment features (233).

FIG. 13 depicts stabilization assembly (116), which is configured to selectively receive coupling sleeve (230). Stabilization assembly (116) includes a bushing (222) configured to fit within the bore in upright portion (110) of skull clamp (100). In some versions an O-ring can be positioned around an outer perimeter of bushing (222) and between the bore of upright portion (110) and bushing (222). A distal cap (224) is connected with bushing (222) by way of a pinned connection. Cap (224) includes a bore and extending within the bore is a holder (225) configured to receive a stabilization feature such as a skull pin.

At the proximal side of stabilization assembly (116) is body (226) with star-shaped recess (221). Body (226) has a threaded portion (227) that threadably engages with a threaded portion (228) within bushing (222). In some versions an O-ring can be positioned between an outer perimeter of bushing (222) and body (226). Elongated bit (130) of applicator (200) engages with recess (221) of body (226) and can rotate body (226) such that body (226) translates longitudinally based on its threaded connection with bushing (222). Body (226) is further configured to receive holder (225). In the illustrated version, holder (225) has an open proximal end that is configured to receive an extension feature (240) of body (226). A fastener (229) connects holder (225) with body (226) via the extension feature (240). In some versions, between holder (225) and body (226) a spacer may be used. As mentioned, holder (225) is configured to receive a stabilizing feature such as a skull pin. Furthermore, holder (225) is configured to translate relative to cap (224) when driven distally by rotation of body (226) such that the attached stabilization feature advances distally toward the head of the patient supported within skull clamp (100).

Body (226) has a lip (242) at its proximal end. Lip (242) is configured to selectively engage with latch members (234) of attachment features (233) of coupling sleeve (230). For instance, latch members (234) are configured with a sloped surface such that advancing coupling sleeve (230) distally when latch members (234) are contacting a proximal-most surface of body (226) causes attachment features (233) to deflect. This deflection allows latch member (234) to travel over lip (242) and then to return to the undeflected state once past lip (242) to make a selective yet secure connection between coupling sleeve (230) and body (226). With coupling sleeve (230) attachable with applicator (200), applicator (200) is thus attachable with body (226) by way of coupling sleeve (230).

Applicator (200) with connected coupling sleeve (230) is further removable or detachable from stabilizing assembly (116) as mentioned above. For example, with the resilient nature of attachment features (233), moving applicator (200) with attached coupling sleeve (230) proximally will causes angled surface of lip (242) to contact and deflect latch members (234) and attachment features (233) outward from longitudinal axis (LA). As further proximal movement occurs, latch members (234) travel over lip (242) until attachment features (233) are no longer connected with body (226). As shown in FIG. 13, lip (242) of body (226) is configured such that lip (242) acts as a stop to prevent body (226) from translating distally beyond a certain distance. This is so because lip (242) will ultimately contact a proximal surface of bushing (222). In some other versions, bushing (222) can include a recess at its proximal end where this recess has a matching profile to lip (242). In this manner, body (226) cannot advance distally past the point where lip (242) fits within this recess of bushing (222).

With this exemplary selectively detachable configuration for applicator (200) and skull clamp (100), less material remains with skull clamp (100), which can be beneficial in terms of weight, obstructions, and imaging ability. Additionally, having applicator (200) configured with the components and features for setting the desired torque—as opposed to those components and features being integrated with the stabilizing assembly or skull clamp—and with applicator (200) being removable from stabilizing assembly (116) of skull clamp (100), less material remains with skull clamp (100) after securing the head of the patient, which again provides benefit in terms of at least weight, obstructions, and imaging ability. In view of the teachings herein, other ways to modify or configure applicator (200) so that applicator (200) is selectively detachable from stabilizing assembly (116) of skull clamp (100) will be apparent to those of ordinary skill in the art.

Figure 14:
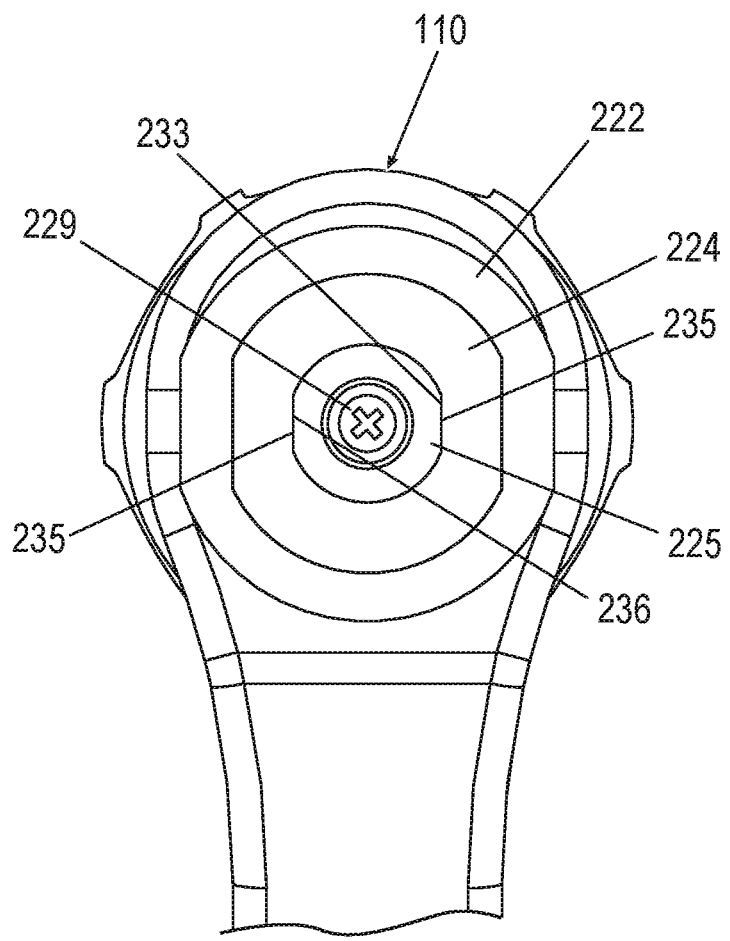
FIG. 14 depicts a front view of the stabilization assembly within an arm of the skull clamp, shown with the stabilization feature removed.

FIG. 14 depicts a front view of stabilization assembly (116) shown with stabilizing feature (250) omitted. As shown and understood from other figures, stabilizing feature (250) is received by holder (225). In the present example, stabilizing feature (250) is slidingly received by holder (225). In this way stabilization feature (250) is able to freely slide into and out of holder (225) when no other objects prevent accessing stabilization feature (250). In other versions stabilization feature (250) could be received within holder (225) by threaded engagement, interference fit, or another engagement type as will be apparent to those of ordinary skill in the art in view of the teachings herein.

As described above, rotation of applicator (200) clockwise is used to rotate body (226) of stabilization assembly (116) clockwise to ultimately tighten or increase the torque applied by stabilization feature (250) to the head of the patient. The threaded engagement that body (226) makes with bushing (222) causes body (226) to translate longitudinally as it rotates. Holder (225) is positioned adjacent to body (226) and fastener (229) creates a contacting or interference fit between portions of body (226) and holder (225). This connection or contact between holder (225) and body (226) is configured such that body (226) can rotate and translate distally relative to bushing (222) while pushing holder (225) distally yet without holder (225) rotating. In this way, when body (226) rotates, the proximal end of holder (225) does not rotate while extension features (240) of body (226) slide along holder (225) as body (226) rotates.

Referring to FIG. 14, stabilization assembly (116) components in the present example are configured with a form fit between cap (224) and holder (225) such that longitudinal translation is the only degree of freedom of movement for holder (225). In one such example, stabilization assembly (116) components are configured with contacting flat sides in some areas to promote this action where holder (225) and associated stabilization feature (250) translates longitudinally without rotation. In use this can be beneficial as it can reduce the tissue and structure trauma the patient may experience at the stabilization contact sites during stabilization. As shown in FIG. 14, holder (225) comprises at least one flat side (235), and in the present example a pair of flat sides (235). Additionally, cap (224) comprises at least one flat side (236), and in the present example a pair of flat sides (236). Flat sides (235, 236) of holder (225) and cap (224) are adjacent and in contact. Additionally, as mentioned above, cap (224) is pinned with stationary bushing (222) such that cap (224) is stationary. With the arrangement of flat sides (235, 236), holder (225) is prevented from rotation despite its contact with rotating body (226). In this way the contact between flat sides (235, 236) ensures that as body (226) rotates, its extension features (240) slide along the proximal portion of holder (225) without causing rotation of holder (225).

As also seen in FIG. 14, cap (224) and bushing (222) also have similarly contacting flat sides. In view of the teachings herein, other ways to configure stabilization assembly (116) such that stabilization features (250) translate without rotation as they are being tightened will be apparent to those of ordinary skill in the art in view of the teachings herein. Additionally, in other versions, stabilization assembly (116) can be configured to permit rotation of stabilizing features (250) during tightening. Again, such modifications to stabilization assembly (116) will be apparent to those of ordinary skill in the art in view of the teachings herein.

In one version, skull clamp (100) and stabilization assemblies (114, 116) are made from radiolucent materials. In such a version, applicator (200) can be made of radiolucent material as well; however, in some other versions applicator (200) is made of at least some materials that are not radiolucent. With the detachability of applicator (200), imagining is not compromised by the materials of construction for applicator (200). It is further contemplated herein that applicator (200) can be usable with devices other than skull clamp (100) and stabilization assembly (116). For instance, applicator (200) could be adapted for use with other fasteners that require applying a torque to the fastener in the range of torque configured to be provided by applicator (200).

When using applicator (200), whether with skull clamp (100) or another structure, a resistance experienced by the user when using applicator (200) to set the predetermined amount of torque remains constant irrespective of the value for the predetermined amount of torque. For instance, the resistance the user experiences when using applicator (200) to set a desire torque is the same regardless if the user sets the torque to 50 newton meters or 100 newton meters. This is unlike torque instruments that use springs to establish torque settings and ranges. Similarly, the resistance experienced by the user when using applicator (200) to set the predetermined amount of torque involves only overcoming frictional forces between moving parts of the device. For instance, there are frictional forces in rotating actuator (150) to translate sleeve (190) along arms (172). Differing torques can be set and in doing so the user experiences the same degree of frictional forces irrespective of the value of the torque being set.

As described above, torque is controlled by varying the bending length of arms (172). Furthermore, the length of the bending length has no impact on the resistance experienced by the user when using applicator (200) to set the predetermined amount of torque. Additionally, when applicator (200) is configured with a positive torque setting, at the same time applicator (200) is configured so that arms (172) are not subject to a bending force. This means that applicator (200) can remain stored with a positive predetermined torque setting without causing strain on the internal components of applicator (200). Again, this differs from torque devices that control torque using one or more springs. With those instruments using a spring control feature, the device must be stored with a zero torque setting to avoid straining the spring over time which then impacts the torque. In the present version described herein, applicator (200) can be set at a positive torque without straining internal components. More specifically this can be achieved by rotating housing (120) while maintaining elongated bit (130) stationary so that arms (172) slide past hook portions (213) as described above. In this orientation, any bending force on arms (172) is removed.

III. Exemplary Detachable Torque Applicator with Sliding Actuator

Figure 15:
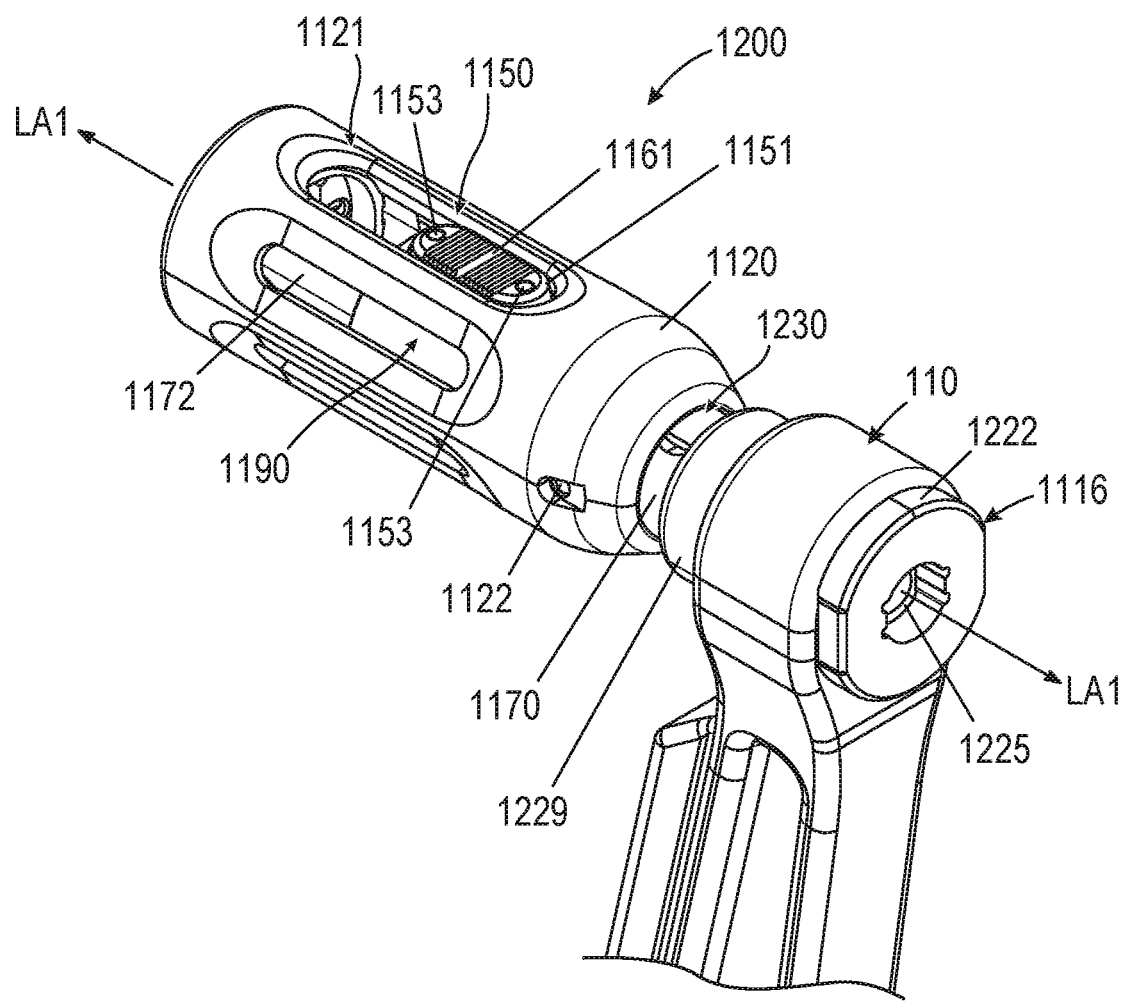
FIG. 15 depicts a perspective view of another exemplary patient head support system showing the skull clamp of FIG. 1 with another stabilization assembly having another detachable torque applicator.
Figure 16:
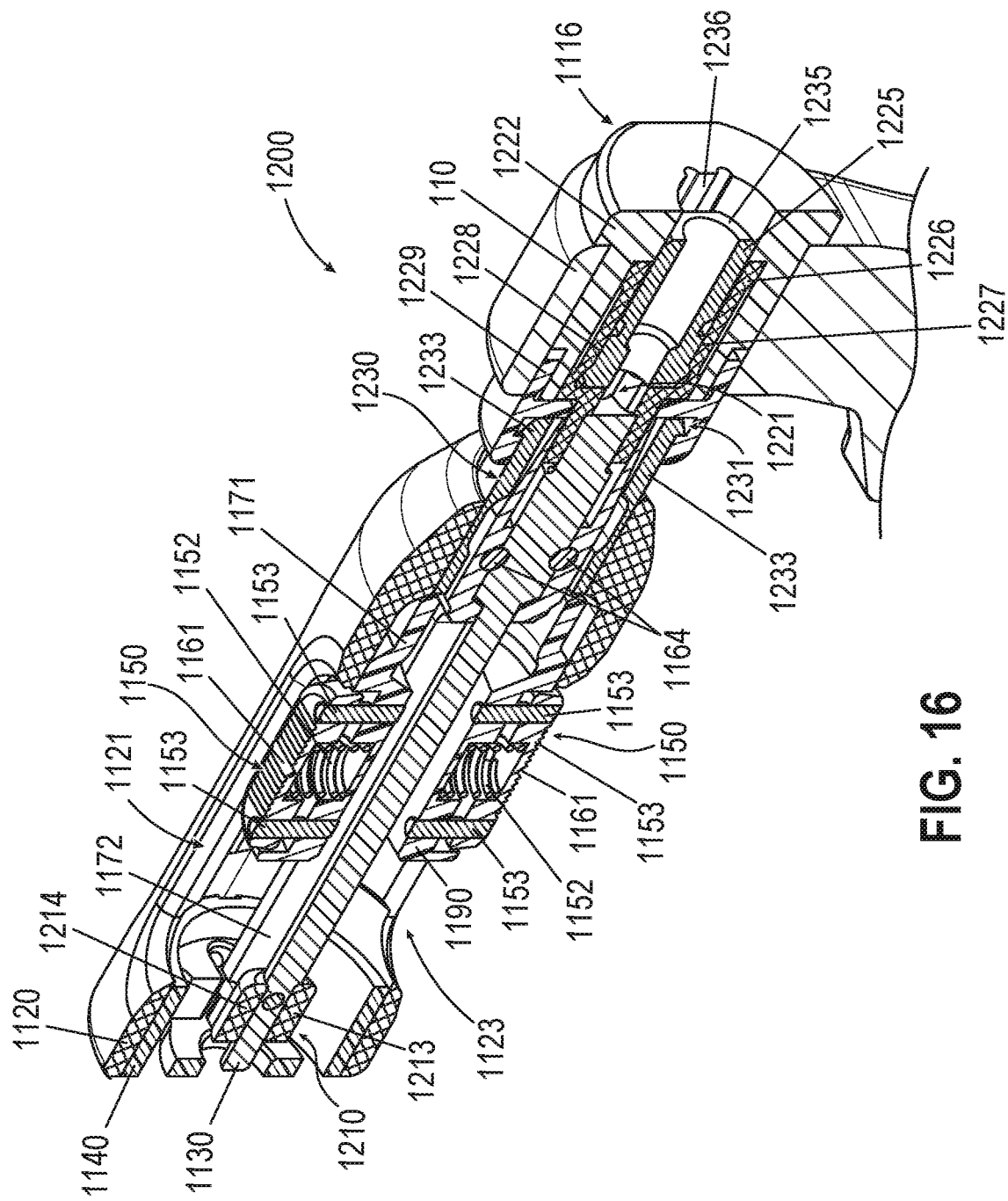
FIG. 16 depicts a cross section view of the stabilization assembly and detachable torque applicator of FIG. 15 taken along line 16-16 of FIG. 15.
Figure 17:
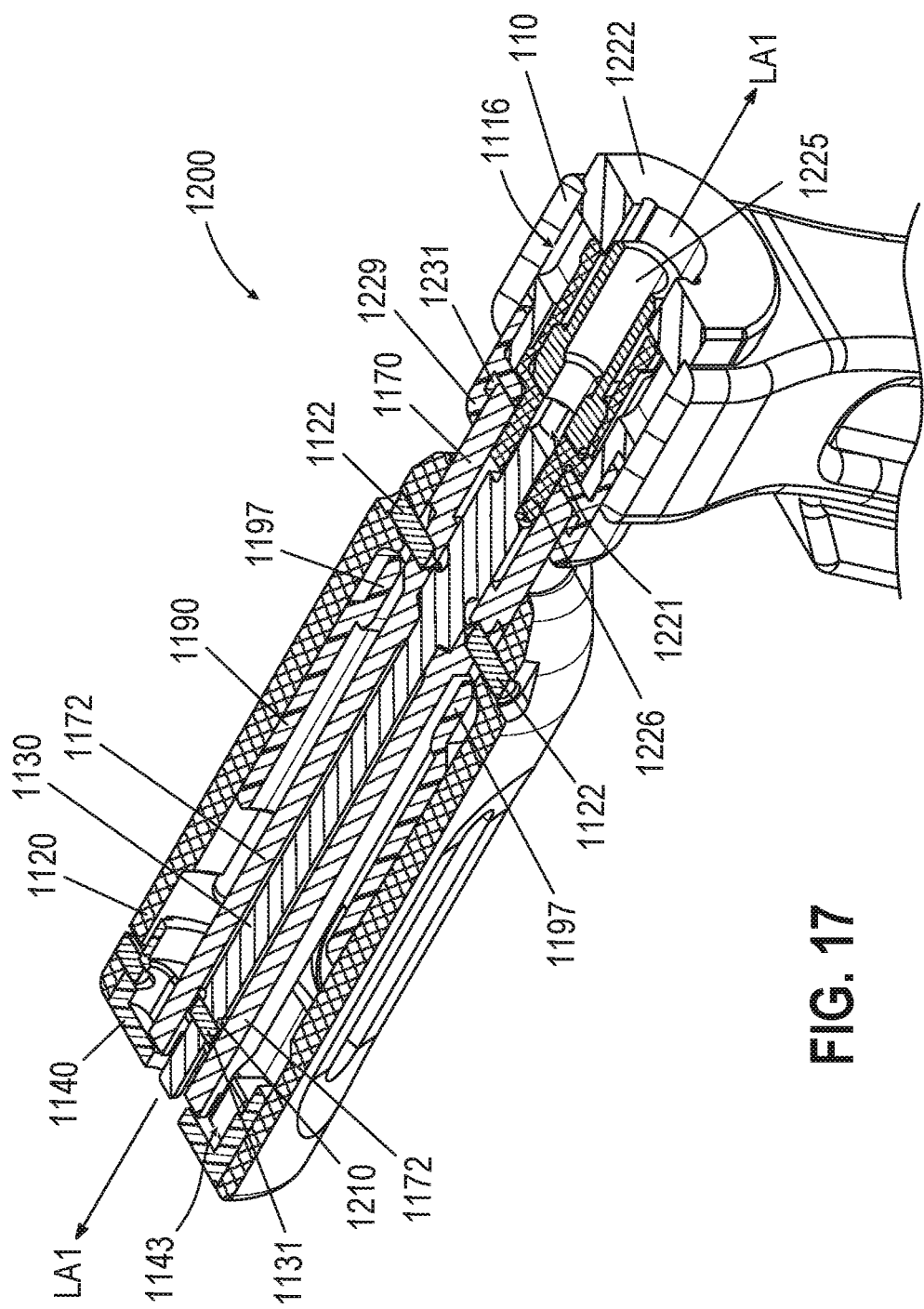
FIG. 17 depicts a cross section view of the stabilization assembly and detachable torque applicator of FIG. 15 taken along line 17-17 of FIG. 15.

FIGS. 15-17 illustrate another exemplary torque applicator (1200) and stabilization assembly (1116) that can be used with head support system (10) in place of torque applicator (200) and stabilization assembly (116). Torque applicator (1200) is sometimes referred to herein simply as applicator (1200). Applicator (1200) includes a housing (1120). Housing (1120) extends longitudinally from a proximal end of applicator (1200) to a distal end of applicator (1200). Housing (1120) further generally defines an outer perimeter of applicator (1200). At the distal end, housing (1120) includes an opening through which an elongated bit (1130) extends. Applicator (1200) defines a longitudinal axis (LA1). Longitudinal axis (LA1) defines a rotational axis about which elongated bit (1130) and other components of applicator (1200) may rotate. In the present example, distal end of elongated bit (1130) has a six-point star shape; however, in other versions distal end of elongated bit (1130) can have other shapes such as slotted, cross, square, among others that will be apparent to those of ordinary skill in the art in view of the teachings herein.

At the proximal end of housing (1120) is a cover (1140) that fits within a proximal opening of housing (1120). In some versions cover (1140) has a snap fit with housing (1120), while in some other versions cover (1140) can be secured to housing (1120) by a pin that extends through housing (1120) and cover (1140). In some versions, cover (1140) includes a plurality of slots that provide visual access within housing (1120). A proximal end of elongated bit (1130) is received within cover (1140).

Housing (1120) also includes lateral openings (1121, 1123). Openings (1121, 1123) are located on opposing sides of housing (1120). Openings (1121, 1123) provide access to an actuator (1150), which can be used to adjust a torque setting for applicator (1200) as will be described in greater detail below. Along an outer surface of housing (1120) there may be other openings or elongated divots that may act as a grip feature to improve gripping ability when grasping torque applicator (1200).

Actuator (1150) in the present example comprises a pair of sliding members (1151) that are located on opposite sides of housing (1120) with one sliding member (1151) located within opening (1121) and another sliding member (1151) located within opening (1123). Sliding members (1151) are configured as depressible features that are slidable when in a depressed state and are stationary when not depressed. On each sliding member (1151) is an indicator (1161) that moves with the sliding member (1151) when sliding members (1151) are moved to adjust a torque setting. In some versions, adjacent to one or both openings (1121, 1123) is a scale of torque settings that are marked on the outer surface of housing (1120). In such versions, indicators (1161) are force indicators by pointing to or associating with the scale. In some versions, the scale can be numeric, while in other versions, the scale can provide relative indication. By way of example only, and not limitation, a relative indication can include a color-coded graphic where one color may indicate an acceptable torque setting while another color or colors may indicate either too low or too high torque settings. In view of the teachings herein, other ways to provide feedback or indication of a torque setting will be apparent to those of ordinary skill in the art.

In some versions, at or near the distal end of housing (1120) is one or more lateral bores configured to each receive a pin (1122) configured to secure a fork member (1170) with housing (1120). Fork member (1170) is a control feature for changing the torque applied by applicator (1200) as will be described in greater detail below. With this exemplary pinned connection with housing (1120), fork member (1170) rotates in unison with housing (1120) as will also be further described below.

Actuator (1150) includes the pair of sliding members (1151) as mentioned above. Additionally, actuator (1150) comprises resilient features such as springs (1152) that connect with sliding members (1151) and allow sliding members (1151) to be depressed to permit sliding movement of sliding members (1151). Positioned within housing (1120) is sleeve (1190). Sleeve (1190) is shown as a tubular structure and connects with sliding members (1151) via one or more pins (1153). In this manner, sleeve (1190) moves in unison with sliding members (1151).

With the above-described configuration where sliding members (1151) of actuator (1150) are positioned within respective openings (1121, 1123) and where sleeve (1190) is connected with sliding members (1151), rotating housing (1120) causes corresponding rotation of actuator (1150) and sleeve (1190). Furthermore, with fork member (1170) connected with housing (1120), rotating housing (1120) causes corresponding rotation of fork member (1170).

Fork member (1170) extends within housing (1120) and includes a distal body portion (1171) and a pair of arms (1172) extending proximally from body portion (1171). Elongated bit (1130) extends through body portion (1171) of fork member (1170), and ultimately emerges from a distal end of housing (1120). Elongated bit (1130) and body portion (1171) of fork member (1170) are configured such that fork member (1170) and elongated bit (1130) can rotate independent of one another. As described further below, such independent rotation occurs when a torque setting or limit is reached and elongated bit (1130) does not rotate with further housing (1120) rotation although fork member (1170) does. Still, under certain conditions elongated bit (1130) and fork member (1170) can rotate in unison. As also described below, this could be the case when a torque setting or limit is not yet reached and elongated bit (1130) rotates in unison with fork member (1170). In the present example, applicator (1200) includes one or more pins (1164) that are located between body portion (1171) of fork member (1170) and elongated bit (1130). Pins (1164) are configured to permit rotation between elongated bit (1130) and fork member (1170) based on the conditions during use of applicator (1200).

As mentioned above, fork member (1170) includes pair of arms (1172) that extend proximally from body portion (1171). At a proximal end, arms (1172) are configured to selectively contact a knob (1210). When the proximal end of arms (1172) contact knob (1210) under certain conditions, arms (1172) bend or deflect away from longitudinal axis (LA1) in response to such contact. However, proximal ends of arms (1172) can contact knob (1210) under other conditions where arms (1172) do not bend or deflect away from longitudinal axis (LA1).

Knob (1210) is positioned about elongated bit (1130) such that bit (1130) extends through knob (1210). Moreover, knob (1210) and elongated bit (1130) are connected by a pin (1131). This connection provides that knob (1210) and elongated bit (1130) rotate in unison. Thus, when knob (1210) rotates, a corresponding rotation of elongated bit (1130) occurs.

Knob (1210) also includes a pair of curved hook features (1213). Proximal end of arms (1172) is configured to contact respective hook features (1213) when fork member (1170) is rotated counterclockwise when viewing applicator (1200) from its proximal end. This is similar to the illustration of FIG. 10A with respect to applicator (200). In this fashion, rotation of fork member (1170) counterclockwise will cause corresponding rotation of knob (1210) and elongated bit (1130) counterclockwise. Moreover, the contact between arms (1172) and hook features (1213) of knob (1210) in this manner occurs without causing bending or deflection of arms (1172) away from longitudinal axis (LA1). Also, proximal ends of arms (1172) are received within respective slots (1143) of cover (1140). Slots (1143) maintain the position of arms (1172) such that arms (1172) do not deflect, i.e., when proximal ends of arms (1172) contact hook features (1213) of knob (1210). Based on the above description, rotation of housing (1120) counterclockwise when viewing applicator (1200) from its proximal end produces a corresponding rotation of elongated bit (1130) in the same direction. This counterclockwise rotation can be considered one condition of use of torque applicator (1200). In at least some instances, rotation in this manner loosens or reduces the contact or engagement of stabilizing feature (250) of stabilizing assembly (1116) with the head of the patient.

Now considering rotation of housing (1120) clockwise when viewed from the proximal end, fork member (1170) will rotate in unison with housing (1120) for the reasons mentioned above. This clockwise rotation causes arms (1172) to move in the same manner. The distance between arms (1172) is smaller than the diameter of knob (1210) across hook features (1213) at its largest point. Consequently, as arms (1172) rotate in this fashion, proximal ends of arms (1172) will contact or engage with an outer curved surface (1214) of hook features (1213). Furthermore, because the distance between the proximal ends of arms (1172) is smaller than the largest diameter point of hook features (1213), the contact of the proximal ends of arms (1172) with outer curved surface (1214) of hook features (1213) causes arms (1172) to adopt a bent or deflected position or state similar to that shown in FIGS. 10B and 10C with respect to applicator (200). Slots (1143) of cover (1140) are elongated to allow deflection of proximal ends of arms (1172) away from longitudinal axis (LA1) when applicator (1200) is in use in this manner.

With this bent or deflected configuration for arms (1172), arms (1172) exert an inward directed force onto hook features (1213) of knob (1210). This creates a holding or squeezing affect where arms (1172) hold or squeeze knob (1210). When the force applied by arms (1172) is higher than the resistance force applied to elongated bit (1130)—based on its engagement with stabilizing assembly (1116) and stabilizing feature's (250) contact with the head of the patient—then rotation of housing (1120) and arms (1172) of fork member (1170) permit arms (1172) to hold knob (1210) with enough force to rotate knob (1210) and connected elongated bit (1130) in unison with arms (1172). In this manner, stabilizing feature (250) of stabilizing assembly (1116) can be tightened by rotating housing (1120) clockwise when viewed from the proximal end of applicator (1200).

When the resistance force applied to elongated bit (1130) —based on its engagement with stabilizing assembly (1116) and stabilizing feature's (250) contact with the head of the patient—is higher than the force arms (1172) are applying to knob (1210), then arms (1172) will slide or slip past hook features (1213) of knob (1210). When arms (1172) slide or slip enough, they resiliently snap back or returning to their relaxed state or undeflected state. In this neutral or relaxed state, arms (1172) are no longer bent or deflected outward from longitudinal axis (LA1). Thus arms (1172) and connected housing (1120) will have rotated, but without corresponding rotation of knob (1210) and elongated bit (1130). So, although further tightening or rotational force may have been applied to housing (1120) and fork member (1170), such further tightening or rotational force is not transferred to knob (1210) and elongated bit (1130) and thus stabilizing assembly (1116) to which elongated bit (1130) is connected with is also not subject to the further tightening or rotational force. This clockwise rotation where knob (1210) rotates can be considered another condition of use of torque applicator (1200), and similarly clockwise rotation where knob (1210) does not rotate can be considered another condition of use of torque applicator (1200).

In the present example of torque applicator (1200), the amount of force exerted or applied on knob (1210) by arms (1172) is a function of a bending length of arms (1172). For instance, arms (1172) are shown having a bending length. Furthermore, applicator (1200) is configured such that the bending length of arms (1172) is adjustable. This adjustment is accomplished by the interaction between sleeve (1190) and arms (1172) of fork member (1170).

Sleeve (1190) includes a portion (1197) that is positioned alongside arms (1172). The bending length can be defined as the length of arms (1172) that extend proximally from portion (1197) of sleeve (1190) to the point where arms (1172) are alongside a distal portion of knob (1210). As mentioned above, translation or sliding of sliding members (1151) of actuator (1150) causes translation of sleeve (1190), which in turn provides the different bending lengths for arms (1172). Thus, the bending length of arms (1172) of fork member (1170) are controlled by a sliding motion of actuator (1150).

As it pertains to torque settings, a smaller bending length is associated with a greater bending force. In other words, as the bending length of arms (1172) becomes shorter, more force is required to bend arms (1172). Similarly, the greater the force would be that is applied to hook features (1213) by arms (1172). Accordingly, in the present version the shortest bending length of arms (1172), and thus the greatest torque setting, would be when sleeve (1190) is translated to its most proximal position. Likewise, the longest bending length of arms (1172), and thus the least torque setting, would be when sleeve (1190) is translated to its most distal position.

In the present version, the bending force is applied based on the interaction between knob (1210) and arms (1172). More specifically, the interaction here is between hook features (1213) of knob (1210) and arms (1172). For example, with a shorter or smaller bending length of arms (1172), based on the position of sleeve (1190), greater force will be required to cause bending of arms (1172) to the point where arms (1172) slide or slip past hook features (1213) of knob (1210) when housing (1120) is rotated clockwise. In other words, applicator (1200) can apply a greater torque to stabilizing assembly (1116) when tightening. In the opposite manner, the longer or greater the bending length of arms (1172), again based on the position of sleeve (1190), less force will be required to cause bending of arms (1172) to the point where arms (1172) slide or slip past hook features (1213) of knob (1210) when housing (1120) is rotated clockwise. In other words, applicator (1200) applies less torque to stabilizing assembly (1116) when tightening.

By way of example only, and not limitation, in one exemplary use applicator (1200) may be adjusted by sliding of actuator (1150) such that the torque indicator reads 60 newton meters. Head support system (10) is configured with a patient's head positioned within skull clamp (100), and with skull clamp (100) having stabilization assemblies (114, 1116) configured with skull pins as stabilizing features (250). Skull clamp (100) is adjusted to move arms (102, 108) so that skull pins contact the head of the patient. Applicator (1200) connects with stabilizing assembly (1116), with elongated bit (1130) engaged with a star-shaped recess (1221) of stabilizing assembly (1116). Housing (1120) of applicator is then rotated in a clockwise manner when viewed from its proximal end. The rotation of housing (1120) causes corresponding rotation of fork member (1170), and cover (1140) as described above. Arms (1172) of fork member (1170) rotate around knob (1210) and ultimately contact outer curved surfaces (1214) of hook features (1213).

Because stabilizing feature (250) of stabilization assembly (1116) has not yet been tightened, it requires less than 60 newton meters of force to tighten them. Consequently, rotating housing (1120) of applicator will tighten the skull pin stabilizing feature (250) connected with stabilizing assembly (1116). This occurs because the proximal ends of arms (1172) engage or contact hook features (1213) of knob and apply sufficient force on knob (1210) to hold and rotate knob (1210) and elongated bit (1130) extending therethrough.

After some tightening, stabilizing feature (250) of stabilizing assembly (1116) requires a force greater than 60 newton meters for further tightening. At this point, rotation of housing (1120) further clockwise again causes arms (1172) of fork member (1170) to rotate. However, the force required to bend arms (1172) away from longitudinal axis (LA1) to the point where arms (1172) will slide or slip along outer curved surfaces (1214) of hook features (1213) is set at 60 newton meters. As mentioned, a torque setting on applicator (1200) greater than 60 newton meters is needed to further tighten stabilizing feature (250). Since in this example the torque setting is at 60 newton meters, rotating housing (1120) will cause arms (1172) to now slide or slip past hook feature (1213). When this occurs, arms (1172) will snap or click back into a neutral undeflected position as arms (1172) clear hook features (1213) such that the bending or deflection force on arms (1172) is removed. This snap or click provides a feedback feature of applicator (1200) that signals to a user that the torque limit has been reached when tightening stabilization feature (250). With this action, knob (1210) and elongated bit (1130) do not rotate with the rotation of housing (1120) and fork member (1170) under these conditions.

If a user of patient head support system (10) decided that greater clamping pressure was desired, the torque setting could be increased by further moving sliding members (1151) of actuator (1150), for example to 100 newton meters. Thereafter, further rotation of housing (1120) of applicator (1200) will rotate arms (1172) such that proximal ends of arms (1172) contact outer curved surface (1214) of hook features (1213) and will bind against hook features (1213) of knob (1210) with enough force to cause rotation of knob (1210) and elongated bit (1130) extending therethrough. Once stabilizing feature (250) of stabilizing assembly (1116) is tightened to the point where it requires a force greater than 100 newton meters to further tighten stabilizing feature (250), then rotation of housing (1120) of applicator (1200) will again rotate arms (1172), but elongated bit (1130) and knob (1210) will apply enough bending force to arms (1172) that arms (1172) will bend and slide or slip past hook features (1213) of knob (1210) instead of gripping and rotating knob (1210).

When the time comes to loosen the stabilizing feature, and possibly remove the patient's head from skull clamp (100), applicator (1200) is engaged with recess (1221) and applicator (1200) is rotated counterclockwise when looking from the proximal end of applicator (1200). With the configuration of arms (1172) and knob (1210), no torque setting adjustment with actuator (1150) and sleeve (1190) is needed before loosening the stabilizing feature. As mentioned above, with the counterclockwise rotation, proximal ends of arms (1172) contact a tip region of hook features (1213) and thereby rotate knob (1210) and elongated bit (1130) irrespective of the bending length configuration of arms (1172) in conjunction with sleeve (1190). The above descried example is merely exemplary. In view of the teachings herein, those of ordinary skill in the art will appreciate other ways to use the devices and systems shown and described herein to securely stabilizing the head of a patient at a known clamping force without exceeding the desired clamping force.

In addition to the bending forces on arms (1172) described above, and the impact arms (1172) have on gripping or applying force to knob (1210) to either rotate knob (1210) or slip past features of knob (1210), frictional forces also influence applicator's (1200) torque setting and application. For instance, frictional forces exist where proximal ends of arms (1172) contact hook features (1213) of knob (1210). Thus, the threshold at the torque limit where the arms (1172) slide or slip along and past hook features (1213) is a function of the bending force applied to arms (1172) and the frictional force between arms (1172) and hook features (1213) of knob (1210). In some instances, the materials of construction of arms (1172) and/or knob (1210) can be configured or modified to provide greater or lesser friction between these components. In view of the teachings herein, other ways to control and modify the interaction of forces between arms (1172) and hook features (1213) of knob (1210) will be apparent to those of ordinary skill in the art.

Applicator (1200) further includes coupling sleeve (1230) that is configured to connect applicator (1200) with stabilization assembly (1116). In the present example, coupling sleeve (1230) connects with and extends distally from housing (1120) of applicator (1200). Coupling sleeve (1230) includes a pair of attachment features (1233) that are configured as elongated bodies with latch members (1234) that are oriented outward away from longitudinal axis (LA1). Attachment features (1233) are further configured as resilient members such that attachment features (1233) are deflectable either toward or away from longitudinal axis (LA1) depending on the direction from which a force is applied on attachment features (1233).

As mentioned, stabilization assembly (1116) is configured to selectively receive coupling sleeve (1230). Stabilization assembly (1116) includes a bushing (1222) configured to fit within the bore in upright portion (110) of skull clamp (100). Bushing (1222) includes a distal bore and extending within the bore is a holder (1225) configured to receive a stabilization feature such as a skull pin.

At the proximal side of stabilization assembly (1116) are bodies (1226, 1229). Body (1226) includes star-shaped recess (1221). Body (1226) extends within bushing (1222) and body (1226) includes a threaded portion (1227) that threadably engages with a threaded portion (1228) of holder (1225). Body (1226) is configured to rotate and when body (1226) rotates, holder (1225) translates longitudinally without rotating based on its threaded engagement with body (1226).

Body (1229) includes an opening such that star-shaped recess (1221) of body (1226) is accessible through body (1229). Body (1229) further threadably engages with bushing (1222). Body (1229) includes an interior recess (1231) configured to selective receive attachment features (1233) of coupling sleeve (1230) to thereby connect applicator (1200) with stabilization assembly (1116). For instance, attachment features (1233) include angled surfaces that contact body (1229) when moving applicator (1200) towards body (1229) of stabilization assembly (1116). This contact deflects attachment features (1233) such that they can locate within interior recess (1231) of body (1229) to selectively secure applicator (1200) with stabilization assembly (1116). Applicator (1200) is further removable or detachable from stabilizing assembly (1116) as mentioned above. For example, with their resilient nature attachment features (1233) can be depressed inward toward longitudinal axis (LA1). This locates attachment features (1233) within recess (1231) such that they can be freely moved proximally relative to body (1229) and thus separated from body.

With this exemplary selectively detachable configuration for applicator (1200) and skull clamp (100), less material remains with skull clamp (100), which can be beneficial in terms of weight, obstructions, and imaging ability. Additionally, having applicator (1200) configured with the components and features for setting the desired torque—as opposed to those components and features being integrated with the stabilizing assembly or skull clamp—and with applicator (1200) being removable from stabilizing assembly (1116) of skull clamp (100), less material remains with skull clamp (100) after securing the head of the patient, which again provides benefit in terms of at least weight, obstructions, and imaging ability. In view of the teachings herein, other ways to modify or configure applicator (1200) so that applicator (1200) is selectively detachable from stabilizing assembly (1116) of skull clamp (100) will be apparent to those of ordinary skill in the art.

As mentioned, holder (1225) is threadably engaged with body (1226) and also configured to receive stabilization feature (250). In the present example, stabilizing feature (250) is slidingly received by holder (225). In this way stabilization feature (250) is able to freely slide into and out of holder (225) when no other objects prevent accessing stabilization feature (250). In other versions stabilization feature (250) could be received within holder (225) by threaded engagement, interference fit, or another engagement type as will be apparent to those of ordinary skill in the art in view of the teachings herein.

Stabilization assembly (1116) components, in the present example, are configured with a form fit between bushing (1222) and holder (1225) such that longitudinal translation is the only degree of freedom of movement for holder (1225). In one such example, stabilization assembly (1116) components are configured with contacting flat sides in some areas to promote this action where holder (1225) and associated stabilization feature (250) translates longitudinally without rotation. In use this can be beneficial as it can reduce the tissue and structure trauma the patient may experience at the stabilization contact sites during stabilization. By way of example, holder (1225) comprises at least one flat side (1235), and in the present example a pair of flat sides (1235). Additionally, distal opening of bushing (1222) comprises at least one flat side (1236), and in the present example a pair of flat sides (1236). Flat sides (1235, 1236) of holder (1225) and bushing (1222) are adjacent and in contact. With the arrangement of flat sides (1235, 1236), holder (1225) is prevented from rotation despite its contact with rotating body (1226). In this way the contact between flat sides (1235, 1236) ensures that as body (1226) rotates, holder (1225) translates without rotating based on holder's (1225) threaded engagement with body (1226).

In view of the teachings herein, other ways to configure stabilization assembly (1116) such that stabilization features (250) translate without rotation as they are being tightened will be apparent to those of ordinary skill in the art in view of the teachings herein. Additionally, in other versions, stabilization assembly (1116) can be configured to permit rotation of stabilizing features (250) during tightening. Again, such modifications to stabilization assembly (1116) will be apparent to those of ordinary skill in the art in view of the teachings herein. Furthermore, other modifications to applicator (1200) may be apparent to those of ordinary skill in the art in view of the teachings herein. By way of example only, and not limitation, in some versions, applicator (1200) may further incorporate calibration features as described above with respect to applicator (200).

In one version, skull clamp (100) and stabilization assemblies (114, 1116) are made from radiolucent materials. In such a version, applicator (1200) can be made of radiolucent material as well; however, in some other versions applicator (1200) is made of at least some materials that are not radiolucent. With the detachability of applicator (1200), imagining is not compromised by the materials of construction for applicator (1200). It is further contemplated herein that applicator (1200) can be usable with devices other than skull clamp (100) and stabilization assembly (1116). For instance, applicator (1200) could be adapted for use with other fasteners that require applying a torque to the fastener in the range of torque configured to be provided by applicator (1200).

When using applicator (1200), whether with skull clamp (100) or another structure, a resistance experienced by the user when using applicator (1200) to set the predetermined amount of torque remains constant irrespective of the value for the predetermined amount of torque. For instance, the resistance the user experiences when using applicator (1200) to set a desire torque is the same regardless if the user sets the torque to 50 newton meters or 100 newton meters. This is unlike torque instruments that use springs to establish torque settings and ranges. Similarly, the resistance experienced by the user when using applicator (1200) to set the predetermined amount of torque involves only overcoming frictional forces between moving parts of the device. For instance, there are frictional forces in moving actuator (1150) to translate sleeve (1190) along arms (1172). Differing torques can be set and in doing so the user experiences the same degree of frictional forces irrespective of the value of the torque being set.

As described above, torque is controlled by varying the bending length of arms (1172). Furthermore, the length of the bending length has no impact on the resistance experienced by the user when using applicator (1200) to set the predetermined amount of torque. Additionally, when applicator (1200) is configured with a positive torque setting, at the same time applicator (1200) is configured so that arms (1172) are not subject to a bending force. This means that applicator (1200) can remain stored with a positive predetermined torque setting without causing strain on the internal components of applicator (1200). Again, this differs from torque devices that control torque using one or more springs. With those instruments using a spring control feature, the device must be stored with a zero torque setting to avoid straining the spring over time which then impacts the torque. In the present version described herein, applicator (1200) can be set at a positive torque without straining internal components. More specifically this can be achieved by rotating housing (1120) while maintaining elongated bit (1130) stationary so that arms (1172) slide past hook portions (1213) as described above. In this orientation, any bending force on arms (1172) is removed.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for stabilizing a head of a patient during a medical procedure comprises (a) a head fixation device configured to receive the head of the patient, (b) a stabilization assembly connected with the head fixation device, wherein the stabilization assembly is configured to receive a stabilization feature configured to contact the head of the patient, and (c) an applicator connectable with the stabilization assembly, wherein the applicator is configured to transfer torque to the stabilization assembly without exceeding a predetermined amount of torque. The applicator comprises (i) a first member, and (ii) a second member, wherein under a first condition an interaction between the first and second members imparts a bending stress on the first member.

Example 2

The apparatus of Example 1, wherein under a second condition the first member is in a relaxed state without the bending stress on the first member.

Example 3

The apparatus of Example 1, wherein under a second condition the interaction between the first and second members imparts a bending stress on the first member, wherein the bending stress in the second condition differs in degree from the bending stress in the first condition.

Example 4

The apparatus of any one or more of Example 1 through Example 3, wherein the applicator further comprising a third member configured to adjustably set the predetermined amount of torque.

Example 5

The apparatus of Example 4, wherein the third member contacts the first member at different positions longitudinally along the first member based on the set predetermined amount of torque.

Example 6

The apparatus of any one or more of Example 4 through Example 5, wherein contact between the third member and the first member dictates a bending length of the first member, wherein the bending length corresponds to the predetermined amount of torque.

Example 7

The apparatus of any one or more of Example 1 through Example 6, wherein the first member comprises at least one arm extending longitudinally relative to the applicator.

Example 8

The apparatus of Example 7, wherein the first member comprises a pair of arms extending longitudinally relative to the applicator.

Example 9

The apparatus of Example 8, wherein the second member is positioned between the pair of arms, and wherein the pair of arms are configured to selectively contact an outer surface of the second member.

Example 10

The apparatus of any one or more of Example 1 through Example 9, wherein the second member comprises a pair of hook features, wherein the first member is configured to selectively contact the hook features.

Example 11

The apparatus of any one or more of Example 1 through Example 10, wherein the first member is operable to bind against an outer surface of the second member when a torque applied to the stabilization assembly is less than the predetermined torque, such that rotation of the applicator causes corresponding rotation of the second member.

Example 12

The apparatus of any one or more of Example 1 through Example 11, wherein the first member is operable to slide past the second member when a torque applied to the stabilization assembly is equal or greater than the predetermined torque, such that the second member remains stationary upon rotation of the applicator to further tighten the stabilization assembly.

Example 13

The apparatus of any one or more of Example 1 through Example 12, wherein the applicator further comprises a bit configured to engage with the stabilization assembly, wherein the second member connects with the bit, and wherein the second member and the bit are configured to rotate in unison.

Example 14

The apparatus of any one or more of Example 1 through Example 13, wherein the stabilization assembly is configured to translate the stabilization feature without rotation of the stabilization feature.

Example 15

The apparatus of any one or more of Example 1 through Example 14, wherein the applicator defines a rotational axis, and wherein the stabilization assembly is configured to receive the stabilization feature such that the stabilization feature is oriented coaxially with the rotational axis.

Example 16

The apparatus of any one or more of Example 1 through Example 15, wherein the applicator comprises an indicator feature that indicates the predetermined amount of torque.

Example 17

The apparatus of any one or more of Example 1 through Example 16, wherein the stabilization feature comprises a skull pin.

Example 18

The apparatus of any one or more of Example 1 through Example 17, wherein the applicator comprises a housing, and wherein the first member is configured to rotate in unison with the housing.

Example 19

The apparatus of any one or more of Example 1 through Example 18, wherein the applicator is detachably connectable with the stabilization assembly.

Example 20

The apparatus of any one or more of Example 1 through Example 19, wherein the stabilization assembly comprises the stabilization assembly of any one or more of Examples 22 through 27.

Example 21

The apparatus of any one or more of Example 1 through Example 20, wherein the applicator comprises the device of any one or more of Examples 28 through 41.

Example 22

An apparatus for stabilizing a head of a patient during a medical procedure comprises: (a) a head fixation device configured to receive the head of the patient, (b) a stabilization assembly connected with the head fixation device, wherein the stabilization assembly is configured to receive a stabilization feature configured to contact the head of the patient. The stabilization assembly comprises (i) a rotational member, and (ii) a translational member. The apparatus further comprises (c) an applicator configured to rotate the rotational member of the stabilization assembly, wherein the translational member is configured to translate in response to rotation of the rotational member.

Example 23

The apparatus of Example 22, wherein a form fit exists between the rotational member and the translational member such that longitudinal translation is the only degree of freedom for movement for the translation member.

Example 24

The apparatus of any one or more of Example 22 through Example 23, wherein the translational member is threadably engaged with the rotational member.

Example 25

The apparatus of any one or more of Example 22 through Example 24, wherein the applicator is detachable from the stabilization assembly, wherein the rotational member and the translational member remain with the stabilization assembly when the applicator is detached therefrom.

Example 26

The apparatus of any one or more of Example 22 through Example 25, wherein the translational member is configured to receive the stabilization feature, where translation of the translational member causes corresponding translation of the stabilization feature without rotation of the stabilization feature.

Example 27

The apparatus of any one or more of Example 22 through 26, wherein the applicator comprises the device of any one or more of Examples 28 through 41.

Example 28

A device for setting an amount of torque and applying torque to an object, comprises (a) a housing configured for rotation during use to apply torque to the object, (b) a bit extending from the housing, wherein the bit is configured to be received by the object, (c) an actuator, wherein the actuator is configured to set the amount of torque, and (d) one or more arms extending longitudinally within the housing. Further, manipulating the actuator changes a bending length of the one or more arms, wherein the amount of torque applied by the device correlates to the bending length of the one or more arms.

Example 29

The device of Example 28, wherein the actuator is accessible from the housing.

Example 30

The device of any one or more of Example 28 through Example 29, further comprising a body, wherein the actuator is configured to adjust a position of the body relative to the one or more arms. Adjusting the position of the body relative to the one or more arms changes a bending length of the one or more arms, wherein the torque applied by the device correlates to the bending length of the one or more arms.

Example 31

The device of any one or more of Example 28 through Example 30, wherein the actuator is rotatable to adjust and set the amount of torque.

Example 32

The device of Example 31, wherein rotation of the actuator causes longitudinal translation of the body.

Example 33

The device of any one or more of Example 28 through Example 30, wherein the actuator is slidable to adjust and set the amount of torque.

Example 34

The device of Example 33, wherein sliding the actuator causes longitudinal translation of the body.

Example 35

The device of any one or more of Example 28 through Example 34, further comprising a calibration feature configured to adjust the amount of torque the applicator applies.

Example 36

The device of any one or more of Example 28 through Example 35, wherein the bit defines a rotational axis and is configured to be received by at least a portion of the object.

Example 37

The device of any one or more of Example 28 through Example 36, wherein a resistance experienced by a user when using the device to set the amount of torque remains constant irrespective of the value for the amount of torque being set.

Example 38

The device of any one or more of Example 28 through Example 37, wherein a resistance experienced by a user when using the device to set the amount of torque comprises only overcoming frictional forces between moving parts of the device.

Example 39

The device of any one or more of Example 28 through Example 38, wherein the bending length has no impact on the resistance experienced by the user when using the device to set the amount of torque.

Example 40

The device of any one or more of Example 28 through Example 39, wherein the device is configured to have a positive torque setting and at the same time the device is also configured so that the one or more arms are not subject to a bending force.

Example 41

The device of any one or more of Example 28 through Example 40, wherein the device further comprises a knob configured to rotate in unison with the bit, wherein the one or more arms are configured to contact the knob when rotating the housing, wherein contact with the knob applies a bending force to the one or more arms, wherein the knob and bit will remain stationary under a first condition, and wherein the knob and bit will rotate under a second condition.

V. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stabilizing a head of a patient during a medical procedure, the apparatus comprising:
    (a) a head fixation device configured to receive the head of the patient;
    (b) a stabilization assembly connected with the head fixation device, wherein the stabilization assembly is configured to receive a stabilization feature configured to contact the head of the patient, wherein the stabilization assembly comprises:
        (i) a rotational member, and
        (ii) a translational member; and
    (c) an applicator configured to rotate the rotational member of the stabilization assembly, wherein the translational member is configured to translate in response to rotation of the rotational member, wherein the applicator is configured to transfer torque to the stabilization assembly while not exceeding a predetermined amount of torque with continued actuation of the applicator once the predetermined amount of torque has been reached, wherein the applicator comprises
        (i) a first member,
        (ii) a second member, wherein under a first condition an interaction between the first and second members imparts a bending stress on the first member, wherein under the first condition actuation of the second member is configured to cause the applicator to rotate the rotational member of the stabilization assembly,
        (iii) a third member configured to adjustably set the predetermined amount of torque, wherein the third member contacts the first member at different positions longitudinally along the first member based on the set predetermined amount of torque, wherein contact between the third member and the first member dictates a bending length of the first member, wherein the bending length corresponds to the predetermined amount of torque, and
        (iv) one or more slidable members that connect with the third member to translationally adjust the position of the third member relative to the first member to adjust the bending length of the first member and thereby set the amount of torque.

2. The apparatus of claim 1, wherein a form fit exists between the rotational member and the translational member such that longitudinal translation is the only degree of freedom for movement for the translation member.

3. The apparatus of claim 1, wherein the translational member is threadably engaged with the rotational member.

4. The apparatus of claim 1, wherein the applicator is detachable from the stabilization assembly, wherein the rotational member and the translational member remain with the stabilization assembly when the applicator is detached therefrom.

5. The apparatus of claim 1, wherein the translational member is configured to receive the stabilization feature, where translation of the translational member causes corresponding translation of the stabilization feature without rotation of the stabilization feature.

6. The apparatus of claim 1, wherein under a second condition the first member is in a relaxed state without the bending stress on the first member.

7. The apparatus of claim 1, wherein under a second condition the interaction between the first and second members imparts a bending stress on the first member, wherein the bending stress in the second condition differs in degree from the bending stress in the first condition.

8. The apparatus of claim 1, wherein the first member comprises at least one arm extending longitudinally relative to the applicator.

9. The apparatus of claim 1, wherein the first member comprises a pair of arms extending longitudinally relative to the applicator, wherein the second member is positioned between the pair of arms, and wherein the pair of arms are configured to selectively contact an outer surface of the second member.

10. The apparatus of claim 1, wherein the second member comprises a pair of hook features, wherein the first member is configured to selectively contact the hook features.

11. The apparatus of claim 1, wherein the first member is operable to bind against an outer surface of the second member when a torque applied to the stabilization assembly is less than the predetermined torque, such that rotation of the applicator causes corresponding rotation of the second member, wherein the first member is operable to slide past the second member when a torque applied to the stabilization assembly is equal or greater than the predetermined torque, such that the second member remains stationary upon rotation of the applicator to further tighten the stabilization assembly.

12. The apparatus of claim 1, wherein the applicator further comprises a bit configured to engage with the stabilization assembly, wherein the second member connects with the bit, and wherein the second member and the bit are configured to rotate in unison.

13. The apparatus of claim 1, comprising
a fourth member configured to calibrate the torque output of the applicator, wherein the fourth member is connectable with the second member to adjust the longitudinal position of the second member relative to the first member to alter the bending length of the first member to match the torque output of the applicator to a reference torque amount to thereby calibrate the torque output of the applicator.

14. The apparatus of claim 13, wherein the first member comprises a pair of arms extending longitudinally relative to the applicator, wherein the second member is positioned between the pair of arms, and wherein the pair of arms are configured to selectively contact an outer surface of the second member.

15. The apparatus of claim 13, wherein the first member is operable to bind against an outer surface of the second member when a torque applied to the stabilization assembly is less than the predetermined torque, such that rotation of the applicator causes corresponding rotation of the second member, wherein the first member is operable to slide past the second member when a torque applied to the stabilization assembly is equal or greater than the predetermined torque, such that the second member remains stationary upon rotation of the applicator to further tighten the stabilization assembly.

* * * * *